US009885672B2

(12) United States Patent
Forutanpour et al.

(10) Patent No.: US 9,885,672 B2
(45) Date of Patent: Feb. 6, 2018

(54) METHODS AND SYSTEMS FOR DETECTING SCREEN COVERS ON ELECTRONIC DEVICES

(71) Applicant: ecoATM, Inc., San Diego, CA (US)

(72) Inventors: Babak Forutanpour, San Diego, CA (US); Jeffrey Ploetner, San Diego, CA (US)

(73) Assignee: ecoATM, Inc., San Diego, CA (US)

( * ) Notice: Subject to any disclaimer, the term of this patent is extended or adjusted under 35 U.S.C. 154(b) by 30 days.

(21) Appl. No.: 15/176,975

(22) Filed: Jun. 8, 2016

(65) Prior Publication Data
US 2017/0356857 A1 Dec. 14, 2017

(51) Int. Cl.
*G06K 9/00* (2006.01)
*G01N 21/958* (2006.01)
*G01N 21/88* (2006.01)
*G06T 7/00* (2017.01)

(52) U.S. Cl.
CPC ....... *G01N 21/958* (2013.01); *G01N 21/8803* (2013.01); *G06T 7/0004* (2013.01); *G06T 7/0085* (2013.01); *G06T 2207/30121* (2013.01)

(58) Field of Classification Search
CPC .......... G06F 2200/1634; G06F 1/1677; G06F 3/0416; G06F 2203/04803; G01N 21/958; G01N 21/8803; G06T 7/0004; G06T 7/0085; G06T 2207/30121
USPC ........................................................ 382/141
See application file for complete search history.

(56) References Cited

U.S. PATENT DOCUMENTS

| 3,808,439 | A | 4/1974 | Renius |
| 4,248,334 | A | 2/1981 | Hanley et al. |
| 4,519,522 | A | 5/1985 | McElwee |
| 4,715,709 | A | 12/1987 | Sekine et al. |
| 4,821,118 | A | 4/1989 | Lafreniere |
| 4,870,357 | A | 9/1989 | Young et al. |
| 4,878,736 | A | 11/1989 | Hekker et al. |
| 4,927,051 | A | 5/1990 | Falk et al. |

(Continued)

FOREIGN PATENT DOCUMENTS

| CN | 1365479 A1 | 8/2002 |
| CN | 2708415 A1 | 7/2005 |

(Continued)

OTHER PUBLICATIONS

2006 Florida Statutes Title XXXIII, Chapter 538, Sections 538.03 and 538.04, 7 pages.

(Continued)

*Primary Examiner* — Kanjibhai Patel
(74) *Attorney, Agent, or Firm* — Perkins Coie LLP

(57) ABSTRACT

Systems and methods for detecting the presence or absence of screen covers on electronic device screens are disclosed. In one embodiment, the method includes obtaining an image of a front side of an electronic device and automatically identifying line segments in the image. For each identified line segment, the method includes calculating the angle of the identified line segment. The method further includes determining an amount of the line segments having vertical or horizontal orientations. If the amount of identified vertical or horizontal line segments exceeds a predetermined threshold amount, then the presence of a screen cover is indicated.

26 Claims, 6 Drawing Sheets

(56) References Cited

U.S. PATENT DOCUMENTS

| | | |
|---|---|---|
| 4,951,308 A | 8/1990 | Bishop et al. |
| 5,027,074 A | 6/1991 | Haferstat |
| 5,077,462 A | 12/1991 | Newell et al. |
| 5,091,773 A | 2/1992 | Fouche et al. |
| 5,105,149 A | 4/1992 | Tokura |
| 5,216,502 A | 6/1993 | Katz |
| 5,280,170 A | 1/1994 | Baldwin |
| 5,339,096 A | 8/1994 | Beaufort et al. |
| 5,419,438 A | 5/1995 | Squyres et al. |
| 5,436,554 A | 7/1995 | Decker |
| 5,570,920 A | 11/1996 | Crisman et al. |
| 5,572,444 A | 11/1996 | Lentz et al. |
| 5,610,710 A | 3/1997 | Canfield et al. |
| 5,717,780 A | 2/1998 | Mitsumune et al. |
| 5,747,784 A | 5/1998 | Walter et al. |
| 5,775,806 A | 7/1998 | Allred |
| 5,839,058 A | 11/1998 | Phillips et al. |
| 5,920,338 A | 7/1999 | Katz |
| 5,949,901 A | 9/1999 | Nichani et al. |
| 5,965,858 A | 10/1999 | Suzuki et al. |
| 5,966,654 A | 10/1999 | Croughwell et al. |
| 5,987,159 A | 11/1999 | Nichani |
| 5,988,431 A | 11/1999 | Roe |
| 6,029,851 A | 2/2000 | Jenkins et al. |
| 6,041,229 A | 3/2000 | Turner |
| 6,181,805 B1 | 1/2001 | Koike et al. |
| 6,228,008 B1 | 5/2001 | Pollington et al. |
| 6,259,827 B1 | 7/2001 | Nichani |
| 6,264,104 B1 | 7/2001 | Jenkins et al. |
| 6,330,354 B1 | 12/2001 | Companion et al. |
| 6,330,958 B1 | 12/2001 | Ruskin et al. |
| 6,393,095 B1 | 5/2002 | Robinson |
| 6,462,644 B1 | 10/2002 | Howell et al. |
| 6,529,837 B1 | 3/2003 | Kang |
| 6,535,637 B1 | 3/2003 | Wootton et al. |
| 6,573,886 B1 * | 6/2003 | Lehtinen .............. G06F 1/1626 345/173 |
| 6,587,581 B1 | 7/2003 | Matsuyama et al. |
| 6,595,684 B1 | 7/2003 | Casagrande et al. |
| 6,633,377 B1 | 10/2003 | Weiss et al. |
| 6,667,800 B1 | 12/2003 | Larsson et al. |
| 6,754,637 B1 | 6/2004 | Stenz |
| 6,758,370 B2 | 7/2004 | Cooke et al. |
| 6,798,528 B1 | 9/2004 | Hartman |
| 6,822,422 B2 | 11/2004 | Sagawa |
| 6,842,596 B2 | 1/2005 | Morii et al. |
| 6,854,656 B2 | 2/2005 | Matsumori |
| 7,069,236 B1 | 6/2006 | Tsunenari |
| 7,076,449 B2 | 7/2006 | Tsunenari et al. |
| 7,178,720 B1 | 2/2007 | Strubbe et al. |
| 7,234,609 B2 | 6/2007 | DeLazzer et al. |
| 7,251,458 B2 | 7/2007 | O'Connell |
| 7,268,345 B2 | 9/2007 | Schultz |
| 7,334,729 B2 | 2/2008 | Brewington |
| 7,520,666 B2 | 4/2009 | Pevzner et al. |
| 7,567,344 B2 | 7/2009 | LeBlanc et al. |
| 7,646,193 B2 | 1/2010 | Suzuki et al. |
| 7,649,450 B2 | 1/2010 | Campion et al. |
| 7,702,108 B2 | 4/2010 | Amon et al. |
| 7,735,125 B1 | 6/2010 | Alvarez et al. |
| 7,761,331 B2 | 7/2010 | Low et al. |
| 7,783,379 B2 | 8/2010 | Beane et al. |
| 8,010,402 B1 | 8/2011 | Sharma et al. |
| 8,019,588 B1 | 9/2011 | Wohlberg et al. |
| 8,025,229 B2 | 9/2011 | Hammond et al. |
| 8,031,930 B2 | 10/2011 | Wang et al. |
| 8,107,243 B2 | 1/2012 | Guccione et al. |
| 8,112,325 B2 | 2/2012 | Foy et al. |
| 8,195,511 B2 | 6/2012 | Bowles et al. |
| 8,254,883 B2 | 8/2012 | Uchida |
| 8,266,008 B1 | 9/2012 | Siegel et al. |
| 8,463,646 B2 | 6/2013 | Bowles et al. |
| 8,718,717 B2 | 5/2014 | Vaknin et al. |
| 8,743,215 B1 | 6/2014 | Lee |
| 8,824,136 B1 * | 9/2014 | Interian, III .......... G06F 1/1632 345/168 |
| 9,043,026 B2 | 5/2015 | Lien et al. |
| 9,582,101 B2 * | 2/2017 | Chang ................. G06F 1/1677 |
| 9,595,238 B2 * | 3/2017 | Won ..................... G09G 5/006 |
| 2001/0039531 A1 | 11/2001 | Aoki |
| 2002/0014577 A1 | 2/2002 | Ulrich et al. |
| 2002/0035515 A1 | 3/2002 | Moreno |
| 2002/0067184 A1 | 6/2002 | Smith et al. |
| 2002/0087413 A1 | 7/2002 | Mahaffy et al. |
| 2002/0129170 A1 | 9/2002 | Moore et al. |
| 2002/0157033 A1 | 10/2002 | Cox |
| 2002/0162966 A1 | 11/2002 | Yoder |
| 2002/0186878 A1 | 12/2002 | Hoon et al. |
| 2003/0006277 A1 | 1/2003 | Maskatiya et al. |
| 2003/0036866 A1 | 2/2003 | Nair et al. |
| 2003/0061150 A1 | 3/2003 | Kocher |
| 2003/0146898 A1 | 8/2003 | Kawasaki et al. |
| 2003/0170529 A1 | 9/2003 | Sagawa |
| 2003/0197782 A1 | 10/2003 | Ashe et al. |
| 2003/0204289 A1 | 10/2003 | Banerjee et al. |
| 2004/0012825 A1 | 1/2004 | Tesavis |
| 2004/0114153 A1 | 6/2004 | Andersen et al. |
| 2004/0141320 A1 | 7/2004 | Bock et al. |
| 2004/0150815 A1 | 8/2004 | Sones et al. |
| 2004/0156557 A1 | 8/2004 | Van Der Weij |
| 2004/0156667 A1 | 8/2004 | Berger et al. |
| 2004/0186744 A1 | 9/2004 | Lux |
| 2004/0205015 A1 | 10/2004 | DeLaCruz |
| 2004/0235513 A1 | 11/2004 | O'Connell |
| 2004/0242216 A1 | 12/2004 | Boutsikakis |
| 2004/0262521 A1 | 12/2004 | Devitt et al. |
| 2005/0128551 A1 | 6/2005 | Yang |
| 2005/0143149 A1 | 6/2005 | Becker et al. |
| 2005/0167620 A1 | 8/2005 | Cho et al. |
| 2005/0187657 A1 | 8/2005 | Hashimoto et al. |
| 2005/0216120 A1 | 9/2005 | Rosenberg et al. |
| 2005/0222690 A1 | 10/2005 | Wang et al. |
| 2005/0231595 A1 | 10/2005 | Wang et al. |
| 2005/0240958 A1 | 10/2005 | Nguyen et al. |
| 2006/0038114 A9 | 2/2006 | Cofer et al. |
| 2006/0167580 A1 | 7/2006 | Whittier |
| 2006/0184379 A1 | 8/2006 | Tan et al. |
| 2006/0195384 A1 | 8/2006 | Bauer et al. |
| 2006/0229108 A1 | 10/2006 | Cehelnik |
| 2006/0235747 A1 | 10/2006 | Hammond et al. |
| 2006/0261931 A1 | 11/2006 | Cheng |
| 2006/0271431 A1 | 11/2006 | Wehr et al. |
| 2006/0279307 A1 | 12/2006 | Wang et al. |
| 2006/0280356 A1 | 12/2006 | Yamagishi |
| 2007/0013124 A1 | 1/2007 | Graef et al. |
| 2007/0057815 A1 | 3/2007 | Foy et al. |
| 2007/0129906 A1 | 6/2007 | Stoecker et al. |
| 2007/0133844 A1 | 6/2007 | Waehner et al. |
| 2007/0140310 A1 | 6/2007 | Rolton et al. |
| 2007/0150403 A1 | 6/2007 | Mock et al. |
| 2007/0205751 A1 | 9/2007 | Suzuki et al. |
| 2007/0263099 A1 | 11/2007 | Motta et al. |
| 2007/0281734 A1 | 12/2007 | Mizrachi |
| 2008/0004828 A1 | 1/2008 | Mizrachi |
| 2008/0027581 A1 | 1/2008 | Saether et al. |
| 2008/0033596 A1 | 2/2008 | Fausak et al. |
| 2008/0097770 A1 | 4/2008 | Low et al. |
| 2008/0109746 A1 | 5/2008 | Mayer |
| 2008/0111989 A1 | 5/2008 | Dufour et al. |
| 2008/0149720 A1 | 6/2008 | Colville |
| 2008/0177598 A1 | 7/2008 | Davie |
| 2008/0207198 A1 | 8/2008 | Juric |
| 2008/0231113 A1 | 9/2008 | Guccione et al. |
| 2008/0255901 A1 | 10/2008 | Carroll et al. |
| 2008/0256008 A1 | 10/2008 | Kwok |
| 2008/0281691 A1 | 11/2008 | Pearson et al. |
| 2008/0296374 A1 | 12/2008 | Gonen et al. |
| 2008/0303915 A1 | 12/2008 | Omi |
| 2008/0306701 A1 | 12/2008 | Zhong et al. |
| 2009/0051907 A1 | 2/2009 | Li et al. |
| 2009/0078775 A1 | 3/2009 | Giebel et al. |
| 2009/0079388 A1 | 3/2009 | Reddy |
| 2009/0095047 A1 | 4/2009 | Patel et al. |

(56) References Cited

U.S. PATENT DOCUMENTS

| | | |
|---|---|---|
| 2009/0184865 A1 | 7/2009 | Valo et al. |
| 2009/0190142 A1 | 7/2009 | Taylor et al. |
| 2009/0207743 A1 | 8/2009 | Huq et al. |
| 2009/0244285 A1 | 10/2009 | Chathukutty |
| 2009/0247133 A1 | 10/2009 | Holmen et al. |
| 2009/0251815 A1 | 10/2009 | Wang et al. |
| 2009/0262341 A1 | 10/2009 | Konopa et al. |
| 2009/0265035 A1 | 10/2009 | Jenkinson et al. |
| 2009/0299543 A1 | 12/2009 | Cox et al. |
| 2009/0312009 A1 | 12/2009 | Fishel |
| 2009/0321511 A1 | 12/2009 | Browne |
| 2010/0005004 A1 | 1/2010 | Hudak et al. |
| 2010/0063894 A1 | 3/2010 | Lundy |
| 2010/0088192 A1 | 4/2010 | Bowles et al. |
| 2010/0110174 A1 | 5/2010 | Leconte |
| 2010/0115887 A1 | 5/2010 | Schroeder et al. |
| 2010/0147953 A1 | 6/2010 | Barkan |
| 2010/0157280 A1 | 6/2010 | Kusevic et al. |
| 2010/0161397 A1 | 6/2010 | Gauthier et al. |
| 2010/0169231 A1 | 7/2010 | Bowles et al. |
| 2010/1085506 | 7/2010 | Wolff |
| 2010/0219234 A1 | 9/2010 | Forbes |
| 2010/0228676 A1 | 9/2010 | Librizzi et al. |
| 2010/0235198 A1 | 9/2010 | Fini et al. |
| 2010/0237854 A1 | 9/2010 | Kumhyr et al. |
| 2010/0262481 A1 | 10/2010 | Baker et al. |
| 2011/0043628 A1 | 2/2011 | Yun |
| 2011/0060641 A1 | 3/2011 | Grossman et al. |
| 2011/0067520 A1 | 3/2011 | Ihrke et al. |
| 2011/0235853 A1 | 9/2011 | Bowles et al. |
| 2012/0016518 A1 | 1/2012 | Saario et al. |
| 2012/0029985 A1 | 2/2012 | Wilson et al. |
| 2012/0030097 A1 | 2/2012 | Hagan et al. |
| 2012/0054113 A1 | 3/2012 | Jayaraman et al. |
| 2012/0063501 A1 | 3/2012 | Aguren |
| 2012/0078413 A1 | 3/2012 | Baker, Jr. |
| 2012/0116928 A1 | 5/2012 | Gventer et al. |
| 2012/0116929 A1 | 5/2012 | Gventer et al. |
| 2012/0117001 A1 | 5/2012 | Gventer et al. |
| 2012/0127307 A1 | 5/2012 | Hassenzahl |
| 2012/0146956 A1 | 6/2012 | Jenkinson |
| 2012/0191562 A1 | 7/2012 | Bowles et al. |
| 2012/0235812 A1 | 9/2012 | De Mello et al. |
| 2012/0254046 A1 | 10/2012 | Librizzi et al. |
| 2013/0006713 A1 | 1/2013 | Haake et al. |
| 2013/0046611 A1 | 2/2013 | Bowles et al. |
| 2013/0046699 A1 | 2/2013 | Bowles et al. |
| 2013/0124426 A1 | 5/2013 | Bowles et al. |
| 2013/0126741 A1 | 5/2013 | Srivastava et al. |
| 2013/0144797 A1 | 6/2013 | Bowles et al. |
| 2013/0173434 A1 | 7/2013 | Hartman |
| 2013/0181935 A1* | 7/2013 | McKenzie ............... G06F 3/044 345/174 |
| 2013/0191236 A1 | 7/2013 | Bowles |
| 2013/0198089 A1 | 8/2013 | Bowles |
| 2013/0198144 A1 | 8/2013 | Bowles |
| 2013/0226679 A1 | 8/2013 | Bowles |
| 2013/0253700 A1 | 9/2013 | Carson et al. |
| 2013/0275314 A1 | 10/2013 | Bowles |
| 2013/0284805 A1 | 10/2013 | Kraft et al. |
| 2013/0290146 A1 | 10/2013 | West et al. |
| 2013/0297388 A1 | 11/2013 | Kyle, Jr. et al. |
| 2014/0012643 A1 | 1/2014 | Behrisch |
| 2014/0067710 A1 | 3/2014 | Gventer et al. |
| 2014/0143161 A1 | 5/2014 | Ahn |
| 2014/0156883 A1 | 6/2014 | Bowles |
| 2014/0214505 A1 | 7/2014 | Shuster-Arechiga et al. |
| 2014/0347473 A1 | 11/2014 | Wolff et al. |
| 2015/0006281 A1 | 1/2015 | Takahashi |
| 2015/0066677 A1 | 3/2015 | Bowles et al. |
| 2015/0120485 A1 | 4/2015 | Nash |
| 2015/0278529 A1* | 10/2015 | Cho ..................... G06F 1/1677 345/668 |
| 2016/0091549 A1 | 3/2016 | Snook et al. |
| 2016/0092849 A1 | 3/2016 | Cirannek et al. |
| 2016/0098688 A1 | 4/2016 | Hunt et al. |
| 2016/0098689 A1 | 4/2016 | Bowles et al. |
| 2016/0098690 A1 | 4/2016 | Silva et al. |
| 2016/0125367 A1 | 5/2016 | Bowles et al. |
| 2016/0125548 A1 | 5/2016 | Bowles et al. |
| 2016/0132840 A1 | 5/2016 | Bowles et al. |
| 2016/0171456 A1 | 6/2016 | Bowles |
| 2016/0171544 A1 | 6/2016 | Heminger et al. |
| 2016/0171575 A1 | 6/2016 | Bowles et al. |
| 2016/0210648 A1 | 7/2016 | Cirannek |
| 2016/0269401 A1 | 9/2016 | Saito et al. |
| 2016/0275460 A1 | 9/2016 | Ploetner et al. |
| 2016/0275518 A1 | 9/2016 | Bowles et al. |
| 2017/0083886 A1 | 3/2017 | Silva et al. |
| 2017/0169401 A1 | 6/2017 | Beane et al. |

FOREIGN PATENT DOCUMENTS

| | | |
|---|---|---|
| CN | 1864088 A1 | 11/2006 |
| CN | 1957320 A1 | 5/2007 |
| CN | 200965706 A1 | 10/2007 |
| CN | 102246384 A1 | 11/2011 |
| CN | 202351953 A1 | 7/2012 |
| CN | 202394296 A1 | 8/2012 |
| CN | 102654927 A1 | 9/2012 |
| CN | 102812500 A1 | 12/2012 |
| CN | 102930642 A1 | 2/2013 |
| CN | 102976004 A1 | 3/2013 |
| CN | 103198562 A1 | 7/2013 |
| CN | 103226870 A1 | 7/2013 |
| CN | 203242065 A1 | 10/2013 |
| CN | 103440607 A1 | 12/2013 |
| CN | 103544772 A1 | 1/2014 |
| CN | 203408902 A1 | 1/2014 |
| CN | 103662541 A1 | 3/2014 |
| CN | 103679147 A1 | 3/2014 |
| CN | 203520502 A1 | 4/2014 |
| CN | 203588366 A1 | 5/2014 |
| CN | 105513201 A1 | 4/2016 |
| EP | 1168253 A1 | 1/2002 |
| EP | 1703436 A1 | 9/2006 |
| GB | 2167553 | 5/1986 |
| JP | 7112801 A1 | 5/1995 |
| JP | 7334583 A1 | 12/1995 |
| JP | 2000121564 A2 | 4/2000 |
| JP | 2002019147 A1 | 1/2002 |
| JP | 2002183286 A1 | 6/2002 |
| JP | 2002259528 A1 | 9/2002 |
| JP | 2002302252 A1 | 10/2002 |
| JP | 2002324264 A1 | 11/2002 |
| JP | 2002358354 A1 | 12/2002 |
| JP | 2003139516 A1 | 5/2003 |
| JP | 2003242243 A1 | 8/2003 |
| JP | 2003264007 A1 | 9/2003 |
| JP | 2003267509 A1 | 9/2003 |
| JP | 2004021569 A1 | 1/2004 |
| JP | 2004288143 A1 | 10/2004 |
| JP | 2004303102 A1 | 10/2004 |
| JP | 2004341681 A1 | 12/2004 |
| JP | 2006127308 A1 | 5/2006 |
| JP | 2006195814 A1 | 7/2006 |
| JP | 2006227764 A1 | 8/2006 |
| JP | 2006260246 A1 | 9/2006 |
| JP | 2007141266 A1 | 6/2007 |
| JP | 2007179516 A1 | 7/2007 |
| JP | 2007265340 A1 | 10/2007 |
| JP | 2008522299 A1 | 6/2008 |
| JP | 2008293391 A1 | 12/2008 |
| JP | 2007086725 A1 | 4/2009 |
| JP | 2009245058 A1 | 10/2009 |
| JP | 2009250971 A1 | 10/2009 |
| JP | 2010177720 A1 | 8/2010 |
| JP | 2012058932 A1 | 3/2012 |
| JP | 2013033361 A1 | 2/2013 |
| JP | 2013037441 A1 | 2/2013 |
| JP | 2013551823 A1 | 8/2013 |
| KR | 20000064168 A1 | 11/2000 |
| KR | 20130085255 A1 | 7/2013 |
| KR | 20140037543 A1 | 3/2014 |

(56) References Cited

FOREIGN PATENT DOCUMENTS

| WO | 115096 A1 | 3/2001 |
|---|---|---|
| WO | 205176 A1 | 1/2002 |
| WO | WO-225613 | 3/2002 |
| WO | 239357 A1 | 5/2002 |
| WO | 3012717 A1 | 2/2003 |
| WO | 3014994 A1 | 2/2003 |
| WO | 2004021114 A1 | 3/2004 |
| WO | 2004114490 A1 | 12/2004 |
| WO | 2005008566 A1 | 1/2005 |
| WO | 2005101346 A1 | 10/2005 |
| WO | 2006058601 A1 | 6/2006 |
| WO | 2006080851 A1 | 8/2006 |
| WO | WO-2007066166 | 6/2007 |
| WO | 9128176 A1 | 10/2009 |
| WO | 2009128173 A1 | 10/2009 |
| WO | 2009129526 A1 | 10/2009 |
| WO | 2010040116 A1 | 4/2010 |
| WO | 2010128267 A1 | 11/2010 |
| WO | 2010128315 A1 | 11/2010 |
| WO | 2011131016 A1 | 10/2011 |
| WO | 2012138679 A1 | 10/2012 |
| WO | 2013074819 A1 | 5/2013 |
| WO | WO-2014075055 | 5/2014 |
| WO | 2015022409 A1 | 2/2015 |

OTHER PUBLICATIONS

Aftermarket Cellular Accessories, "Cellular Phone Model Identification," retrieved from http://web/archive.org/web/20060328064957/http://aftermarketcellular.com/ic/identification.html on Mar. 16, 2014, published Mar. 28, 2006, 3 pages.
Altec Lansing User's Guide 2007, 8 pages.
Bussiness Wire, "The World's First Office Photography Machine" at CES 2008 Launched by Ortery Technologies, Jan. 7, 2008, 3 pages.
CNET, "Tackling LCD "burn ins", and dead/stick Pixels", published Sep. 2, 2009, retrieved from http://www.cnet.com/news/tackling-lcd-burn-ins-and-deadstuck-pixels/.
Evgenii Masunov, Mar. 25, 2010, http://www.appleinsider.ru/news/ipone-obladaet-luchshim-tachskrinom-provereno_robotom.html, 4 pages.
Geekanoids, You Tube Video, "Apple iPhone 3GS Unboxing and Review", uploaded on Jun. 19, 2009, retrieved from http://www.youtube.com/watch?v=GCEi9QAeDqk on Sep. 2, 2009.
GSM Arena Glossary, "LCD (Liquid Crystal Display", retrieved from http://www.gsmarena.com/glossary.php3?term=lcd on Apr. 28, 2016, 1 page.
Lambert, Emily, "Use It Up, Wear It Out", Forbes 175.5 (2005): 77-78. Business Source Complete. Web. Jan. 6, 2015, 3 pages.

Littleton Partners with Donations Ink (Jan. 19, 2006) US Fed News Service, Including US State News. Web. Jan. 6, 2015, 1 page.
MobileGazette.com, "2006 in Review: The Good, The Bad and the Ugly", published Dec. 2006, retrieved from http://www.mobilegazette.com/2006-review-06x12x22.htm on Nov. 11, 2015.
PC World, "Wipe Your Cell Phone's Memory Before Giving it Away", published Jan. 2006, retrieved from http://www.washingtonpost.com/wp-dyn/content/article/2006/01/30/AR2006013001144.html on Nov. 10, 2015.
Perng et al., "A Novel Vision System for CRT Panel Auto-Inspection", Proceedings of the 2005 IEEE International Conference on Mechatronics, Jul. 10-12, 2005, pp. 4.
Perng et al., "A Novel Vision System for CRT PaNnel Auto-Inspection", Journal of the Chinese Institute of Industrial Engineers, vol. 24, No. 5, pp. 341-350 (2007).
Rawson, Chris, "TUAW: 25 Ways to Check the Hardware on Your iPhone 4", published Aug. 12, 2010, retrieved at http://www.tuaw.com/2010/08/13/hardware-test-your-iphone-4/ on Feb. 28, 2014.
Rehg et al. "Vision for a Smart Kiosk" IEEE, Computer Society Conference on Computer Vision and Pattern Recognition (1997).
Rolf Steinhilper "Remanufacturing: The Ultimate Form of Recycling", Fraunhofer IRBVerlag, 1998, parts 1-3, http://www.reman.org/Publications_main.htm.
SimplySellular, "Get Cash for your Old Cell Phone", published Apr. 2, 2010, retrieved from http://simplysellular.com/conditions.php on Jan. 6, 2015, 2 pages.
Wilson, Doug, "Liquid Crystal Display (LCD) Inspection System", National Instruments Case Study, available May 10, 2009, retrieved from http://sine.ni.com/cs/app/cod/p/id/cs-345 on Jan. 5, 2015, 2 pages.
Yahoo Answers, "What is a Clean ESN?" published Jun. 23, 2009, retrieved from http://web.archive.org/web/20090623215042/http://answers.yahoo.com/question/inde,8020US?qid=20080318061012AANFRco on Apr. 3, 2014.
Co-Pending U.S. Appl. No. 15/130,851 of Forutanpour, B. et al., filed Apr. 15, 2016.
Co-Pending U.S. Appl. No. 15/195,828 of Forutanpour, B. et al., filed Jun. 28, 2016.
Co-Pending U.S. Appl. No. 15/630,508 of Silva, J. et al., filed Jun. 22, 2017.
Co-Pending U.S. Appl. No. 15/630,539 of Bowles, M. et al., filed Jun. 22, 2017.
Investopedia: What's the difference between weighted average accounting and FIFO/LILO accounting methods? Aug. 19, 2010. Accessed via archive.org [https://web.archive.org/web/20100819200402/http://www.investopedia.com/ask/answers/09/weighted-average-fifo-lilo-accounting.asp].

* cited by examiner

METHODS AND SYSTEMS FOR DETECTING SCREEN COVERS ON ELECTRONIC DEVICES

TECHNICAL FIELD

The present disclosure is directed generally to methods and systems for evaluating mobile phones and other consumer electronic devices and, more particularly, to methods and systems associated with detecting screen covers on such devices.

BACKGROUND

It is often necessary to visually evaluate a mobile device (e.g., a smartphone or tablet) to identify cracks or other defects in the mobile device. For example, pricing the mobile device, assessing the mobile device for possible repair, and evaluating the mobile device for warranty coverage may all require identification of any cracks in the mobile device. Individualized manual inspection of mobile devices for cracks is slow, cumbersome, and can yield inconsistent results. Current automated methods for detecting cracks in other contexts are often over-inclusive resulting in high rates of false-positive crack indications. Accordingly, there is a need for improved methods and systems for automatically detecting cracks in mobile devices.

DETAILED DESCRIPTION

Overview

Figure 1:
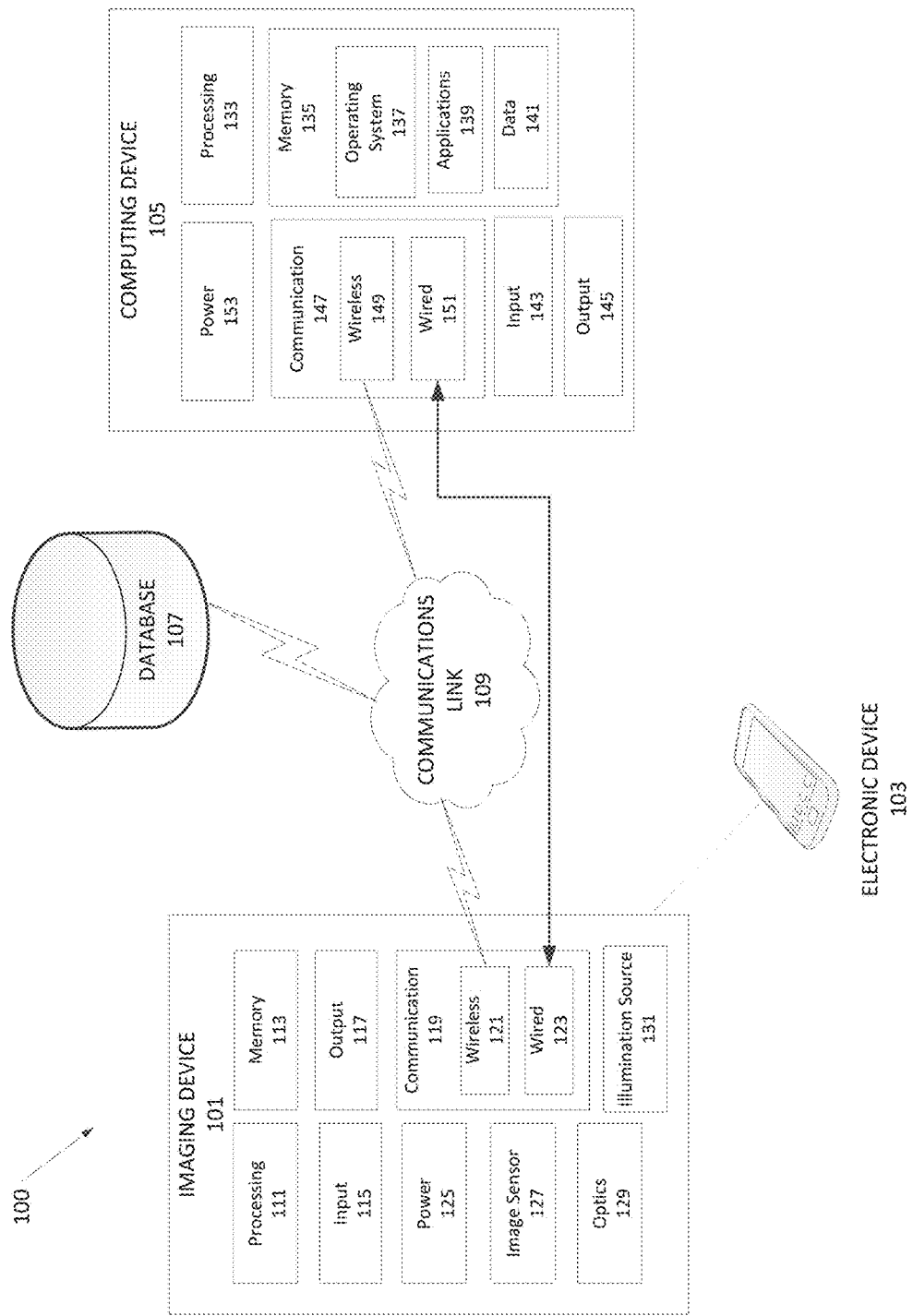
FIG. 1 is a block diagram illustrating components of a suitable computing environment for implementing various aspects of the present technology.

The following disclosure describes systems and methods for automated visual inspection and evaluation of electronic devices. In particular, at least some embodiments of the present technology enable automatic detection of screen covers (alternatively known as screen protectors) on electronic devices. Screen covers have been discovered to produce telling artifacts in digital images. These artifacts include, for example, an abundance of lines that are aligned either horizontally (i.e., parallel to the long edge of the device screen) or vertically (i.e., parallel to the short edge of the device screen), an abundance of lines in the corner regions of the device, and anomalies associated with the presence of bubbles. These artifacts can be exploited to automatically analyze an image of a front side of an electronic device to detect the presence of a screen cover. This can be useful because screen covers tend to interfere with other types of automated device evaluation. For example, edges of screen covers have been discovered to be a source of false-positive crack indications in conventional processes for automated evaluation of electronic devices.

In one embodiment, line segments in an image of an electronic device are automatically identified using machine vision. Next, the angles of the identified line segments can be calculated, including determining the amount of line segments aligned within a predetermined range of a vertical orientation (e.g., within 5 degrees of vertical, within 3 degrees of vertical, etc.) and the amount of line segments aligned within a predetermined range of a horizontal orientation (e.g., within 5 degrees of horizontal, within 3 degrees of horizontal, etc.). If the amount of identified vertical line segments, the amount of identified horizontal line segments, or a combination of these amounts exceeds a predetermined threshold, then the presence of a screen cover is indicated. In addition or alternatively, the amount of line segments located within corner portions of the image is determined, and, if this amount exceeds a predetermined threshold (e.g., over 50% of the identified lines are located in the corner regions), then the presence of a screen cover is indicated or confirmed. Furthermore, the amount of image segments including bright spots associated with the presence of bubbles can be determined, and, if this amount exceeds a predetermined threshold, then the presence of a screen cover is indicated or confirmed.

Certain details are set forth in the following description and in FIGS. 1-5D to provide a thorough understanding of various embodiments of the present technology. In other instances, well-known structures, materials, operations and/or systems often associated with smartphones and other handheld devices, consumer electronic devices, computer hardware, software, and network systems, etc. are not shown or described in detail in the following disclosure to avoid unnecessarily obscuring the description of the various embodiments of the technology. Those of ordinary skill in the art will recognize, however, that the present technology can be practiced without one or more of the details set forth herein, or with other structures, methods, components, and so forth. The terminology used below should be interpreted in the broadest reasonable manner, even though it is being used in conjunction with a detailed description of certain examples of embodiments of the technology. Indeed, certain terms may even be emphasized below; however, any terminology intended to be interpreted in any restricted manner will be specifically defined as such in this Detailed Description section.

The accompanying Figures depict embodiments of the present technology and are not intended to be limiting of the scope of the present technology. The sizes of various depicted elements are not necessarily drawn to scale, and these various elements may be arbitrarily enlarged to improve legibility. Component details may be abstracted in the Figures to exclude details such as the position of components and certain precise connections between such components when such details are unnecessary for a complete understanding of how to make and use the invention.

In the Figures, identical reference numbers may identify identical, or at least generally similar, elements. To facilitate the discussion of any particular element, the most significant digit or digits of any reference number may refer to the Figure in which that element is first introduced. For example, element 101 is first introduced and discussed with reference to FIG. 1.

Detection of Screen Covers on Electronic Device Screens

FIG. 1 illustrates an embodiment of an environment 100 in which various aspects of the present technology can be implemented. The environment 100 includes an imaging device 101 configured to obtain images and/or video of an electronic device 103 (e.g., a mobile phone, tablet, notebook, etc.). The imaging device 101 is in communication with a computing device 105 and a database 107 via a communications link 109.

The imaging device 101 includes a processing component 111, a memory 213, input and output components 115 and 117, and a power component 125. The imaging device 101 further includes an image sensor 127, associated optics 129, and an illumination source 131. A communication component 119 of the imaging device 101 includes a wired connection 123 and a wireless transceiver 121. The computing device 105 can include several components similar to components of the imaging device 101. For example, the computing device 105 can include a processing component 133, memory 135 (which can store an operating system 137, applications 139, and data 141), along with input 143 and output 145 components and a power component 153. A communication component 147 of the computing device 105 includes a wired connection 151 and a wireless transceiver 147. These features of the imaging device 101 and the computing device 105 are described in more detail below in the context of a routine for detecting screen covers in accordance with an embodiment of the present technology.

Figure 2:
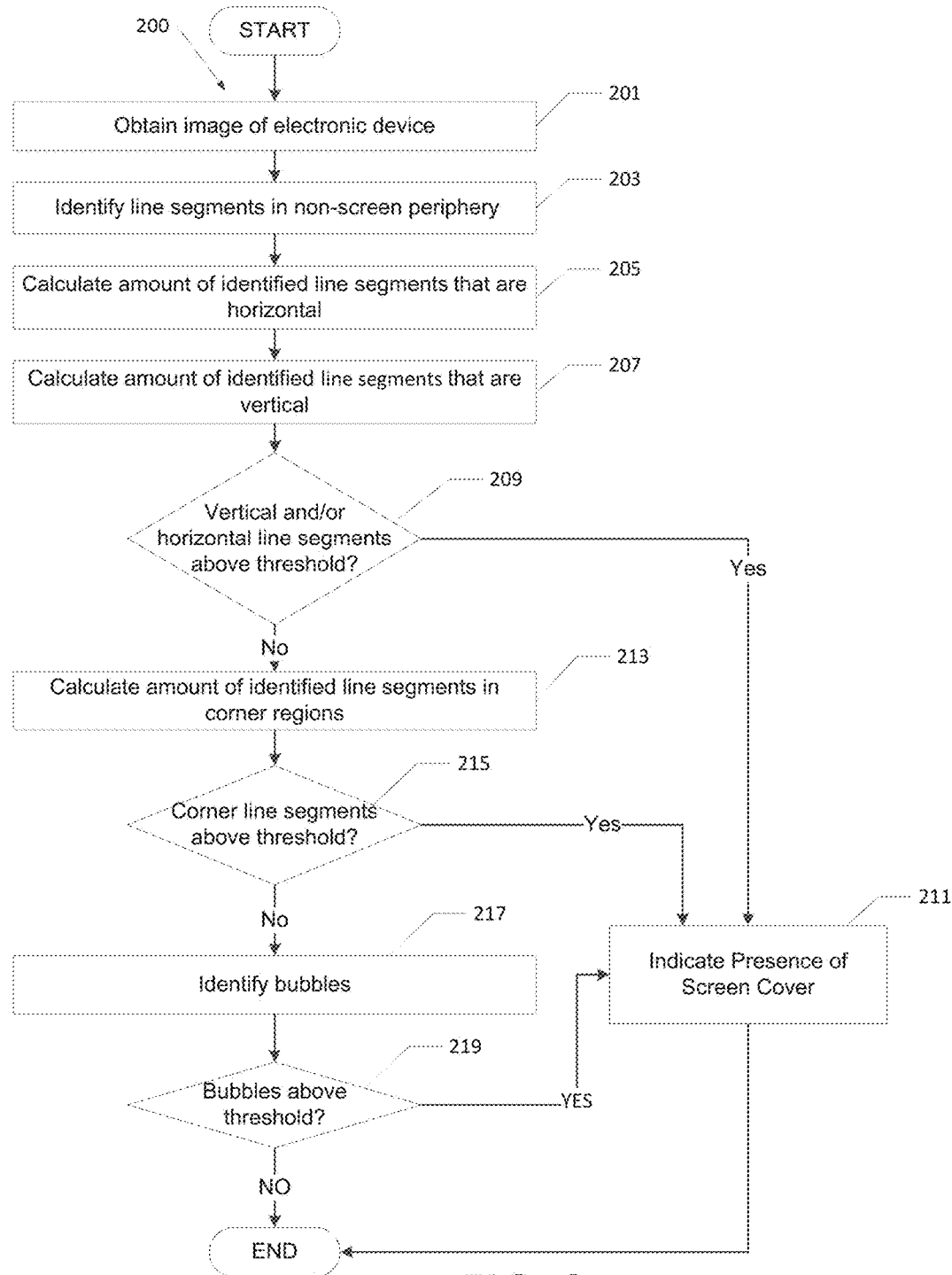
FIG. 2 is a flow diagram of a method for detecting screen covers on electronic device screens in accordance with an embodiment of the present technology.

FIG. 2 is a flow diagram of a routine for detecting screen covers on device screens in accordance with an embodiment of the present technology. In at least some cases, the routine 200 is performed by the computing device 105, which is described in more detail below. In block 201 the routine 200 obtains an image of the electronic device 103. For example, the imaging device 101 can be used to obtain one or more images of the electronic device 103. In some embodiments, the images are included in a video of the electronic device 103. For example, the imaging device 101 can be moved relative to the electronic device 103 or vice versa to obtain different views of the electronic device 103 on the video. A similar approach can be taken using still images, such as by taking a number of still images with the imaging device 101 at different orientations relative to the electronic device 103. For example, the imaging device 101 and/or the electronic device 103 can be affixed to moveable components such as a moveable platform or mounting surface. The moveable components can be controlled and moved using a belt drive, rack and pinion system, or other suitable drive system coupled to an electronic controller (e.g., the computing device 105). Furthermore, the routine 200 can obtain various images of the electronic device 103 under different conditions, for example under different lighting conditions (e.g., no lights on, all lights on, only infrared illumination, etc.), under different operating conditions (e.g., with a display of the electronic device 103 in an "off" mode, with the display in an "on" mode, with the display presenting a predetermined image (e.g. a QR code or other known image), etc.). In other embodiments, the routine 200 can obtain a single image of the electronic device 103 and/or images the electronic device 103 under a single operating condition. With reference again to the routine 200, the image or images obtained by the imaging device 101 can be transmitted to the computing device 105, such as via the communications link 109, for analysis and evaluation.

In some embodiments, the routine first performs a crack detection routine before proceeding to detecting the presence or absence of a screen cover. If there are no cracks found during the crack detection routine, then the screen cover detection process can be bypassed or omitted. If there are cracks found during the crack detection subroutine, then the routine can proceed to detect the presence of a screen cover. As described in more detail below, certain cracks identified during the crack detection process may be attributable to the screen cover rather than genuine cracks. The routine can also first perform a brightness check to determine the average brightness of non-cracked regions of the screen. This brightness level can be compared to the average brightness for that particular model of electronic device. If the brightness level is higher than the average for that model of electronic device by some threshold amount (e.g., at least 10% brighter), then a screen cover is more likely to be present. Accordingly, some or all of the thresholds discussed in more detail below can be adjusted (e.g., loqw in view of the increased likelihood of a screen cover in these circumstances. In some embodiments, the routine can prompt the user to indicate whether a screen cover is present. If the user indicates that a screen cover is present (e.g., input via a touch screen interface, etc.), then some or all of the thresholds discussed in more detail below can be adjusted (e.g., lowered) in view of the increased likelihood of a screen cover in these circumstances.

Prior to proceeding with block 203 to detect a screen cover, the routine 200 can first analyze the image for possible glints that are indicative of true cracks. If such glints are found, then the screen cover detection process can be bypassed and the electronic device 103 can be graded accordingly. For example, the image can be analyzed by counting up all pixels above some threshold value (e.g., above 140 brightness units in a 0-255 range, greater than 150, 160, 170, etc.). If the number of high-brightness pixels is above some threshold number (e.g., greater than 20, 40, 60, 80, etc.), then a glint is identified. Such a high-brightness glint is likely due to an actual crack in the screen of the electronic device 103 reflecting light into the camera, and accordingly the screen cover detection process can be bypassed. Alternatively, the routine 200 can continue to block 203 without first performing this check for glints.

In block 203, the routine 200 applies a line detector to the non-screen periphery of the electronic device image (e.g., a Canny edge detector and/or other suitable image processing algorithms configured to detect line segments). The line detector can be applied to the screen as well as non-screen portions of the image. The output of this line segment detector may indicate cracks in the device screen as well as certain other features that may appear similar to as cracks. For example, these other features can include the perimeter of a screen cover, smudges, fingerprints, reflections, light scratches, etc.

In block 205, the routine 200 calculates the amount of identified line segments that are horizontal. The image of the electronic device can be rotated as needed until the device is square with respect to perpendicular axes (e.g., a horizontal axis that runs parallel to the long edge of the electronic device and a vertical axis that runs parallel to the short edge of the electronic device when the electronic device is positioned with its screen facing the imaging device). For each of the identified line segments from block 203, the routine 200 can assign an orientation vector corresponding to the general direction along which the line segment (or portion of the line segment) is aligned. For example, a given line segment may be oriented at 10 degrees with respect to the horizontal axis. If the orientation of the line segment is within a predetermined angular range of the horizontal axis, then the routine 200 identifies the line segment as "horizontal." The predetermined angular range can vary in different embodiments. For example line segments can be considered horizontal if they are within 10 degrees of the horizontal axis, within 5 degrees, within 4 degrees, within 2 degrees, within 1 degrees, or less. The routine 200 then calculates the amount of identified line segments that are horizontal. In at least some embodiments, the routine 200 counts the number of pixels that fall within line segments that have been identified as horizontal. This pixel count can then be divided by the total number of pixels that fall within any of the identified line segments, resulting in a ratio of horizontal line segments to total line segments for the electronic device screen.

In block 207, the routine calculates the amount of identified line segments that are vertical. This process can be generally similar to the process followed in block 205 for calculating the amount of identified line segments that are horizontal. For example, for each line segment identified in block 203, the routine can identify the line segment as "vertical" if the orientation of the line segment is within a predetermined angular range of the vertical axis. As noted above, this predetermined range can vary, such as within 10 degrees of the vertical axis, within 5 degrees, within 4 degrees, within 2 degrees, within 1 degrees, or less. The routine 200 then calculates the amount of identified line segments that are vertical. In at least some embodiments, the routine 200 counts the number of pixels that fall within line segments that have been identified as vertical. This pixel count may then be divided by the total number of pixels that fall within any of the identified line segments, resulting in a ratio of vertical line segments to total line segments for the electronic device screen. In some embodiments, the routine counts as vertical or horizontal only those lines that exceed a predetermined threshold distance, e.g., at least 35 pixels, at least a number of pixels corresponding to approximately ¼" of the screen, or other suitable threshold distance.

In decision block 209, the routine 200 determines whether the amount of vertical and/or horizontal line segments are above a predetermined threshold. For example, the routine 200 can assess whether the identified line segment are "mostly" horizontal or "mostly" vertical by evaluating whether the ratio of horizontal line segments to total line segments or the ratio of vertical line segments to total line segments exceeds the predetermined threshold. The predetermined threshold can vary in different embodiments, for example if the horizontal ratio or the vertical ratio exceeds 0.25, 0.5, 0.75, or more, the routine 200 determines that the identified line segments are primarily horizontal or primarily vertical, as the case may be. In this case, the routine 200 proceeds to block 211 and indicates the presence of a screen cover. This indication can be provided as input to another process, for example evaluating the electronic device for possible purchase. This indication can be conveyed to a user, for example via a display screen coupled to the computing device 105. For example, the user can be asked to remove the screen cover and re-initiate the process. As noted above, the threshold value for the horizontal ratio or the vertical ratio can be lowered in instances in which the electronic device had an unusually high brightness value in non-cracked regions (indicating an increased likelihood of a screen cover) or if a user indicated that screen cover is present.

If, in block 209, the routine 200 determines that the amount of vertical and/or horizontal line segments is not above the predetermined threshold (i.e., that the identified line segments are not primarily horizontal or primarily vertical), then the routine 200 proceeds to block 213 and calculates the amount of identified line segments in corner regions. Corner regions of the electronic device can be defined as those regions falling within a predetermined distance of both a top edge and a side edge or a bottom edge. In other embodiments, the corner regions can be defined as 4 quarter-circular regions, each with a center positioned corresponding to the physical corners of the electronic device. The space encompassed by the corner regions can vary in different embodiments. In one embodiment, each corner region is defined by the area that is within 5 cm of a horizontal edge of the electronic device and within 5 cm of a vertical edge of the electronic device. In other embodiments, these distances can vary, for example within 10 cm, within 4 cm, within 3 cm, or less.

For each of the identified line segments from block 203, the routine 200 can determine whether the line segment (or any portion of the line segment) falls within one of the designated corner regions. In one embodiment, the routine 200 counts the number of pixels that fall within line segments that have been assessed as falling within the corner regions. In some embodiments, this pixel count is divided by the total number of pixels that fall within any of the identified line segments, resulting in a ratio of corner line segments to total line segments for the electronic device screen.

In decision block 215, the routine determines whether the corner line segments exceeds a predetermined threshold. For example, the routine 200 can assess whether the identified line segments are "mostly" corner line segments by evaluating whether the ratio of corner line segments to total line segments exceeds the predetermined threshold. The predetermined threshold can vary in different embodiments, for example if the corner ratio exceeds 0.25, 0.5, 0.75, or more, the routine 200 determines that the identified line segments are primarily corner line segments. In this case, the routine 200 proceeds to block 211 and indicates the presence of a screen cover. If the routine 200 determines that the identified line segments are not primarily corner line segments (i.e., the ratio of corner line segments does not exceeds the predetermined threshold), then the routine 200 proceeds to block 217. As noted above, the threshold value for the corner ratio can be lowered in instances in which the electronic device had an unusually high brightness value in non-cracked regions (indicating an increased likelihood of a screen cover) or if a user indicated that screen cover is present.

In block 217, the routine 200 identifies any bubbles in the image. Bubbles in the image can be indicative of a screen cover even if the identified horizontal, vertical, and corner line segments did not exceed the thresholds indicated in decision blocks 209 and 215. Any suitable technique can be used to identify bubbles in the image. In one example, identifying bubbles proceeds by evaluating slices or other segments of the image separately from one another, with the slices divided along lines that run parallel to the short axis of the electronic device. In some embodiments, each slice can be approximately 10 pixels wide, or the total number of slices can be approximately 80, though these numbers can vary depending on the resolution of the image, the size of the electronic device, and other factors. If a given slice contains too few pixels (e.g., the slice corresponds to a region of the electronic device in which the majority of the slice is masked from analysis, such as a slice that would overlap the home button), then the slice is excluded from analysis. Next, for each slice, the routine can determine whether the number of high-brightness pixels exceeds a predetermined threshold. "High-brightness pixels" can be, for example, any pixels exceeding a predetermined brightness threshold, for example over 170 brightness units when the entire image has been normalized to an average brightness of 140 brightness units. In one example, if there are more than 15 high-brightness pixels in a given slice, then the bubble detection process can terminate, as this indicates a likely actual crack. If there are not more than 15 high-brightness pixels (i.e., less than the predetermined threshold number of high-brightness pixels) in any of the slices, then the bubble detection routine proceeds.

In some embodiments, the routine looks for bubbles or indicators of bubbles inside the screen region of the device first, for example excluding top, bottom, and side regions of the device external to the screen region. If bubbles are not found in the screen region, then the routine can look for bubbles or indicators of bubbles in top, bottom, and/or side regions of the device outside of the screen region. As noted above, a crack detection routine can be performed before the screen cover detection routine begins. If the number of identified cracks exceeds a predetermined threshold (e.g., more than 75 cracks identified), then the routine can bypass the bubble detection steps. This can mitigate the risk that a badly cracked phone would be improperly classified as having bubbles due to the effect of multiple cracks blurring into white regions when the image is blurred. In some embodiments, the bubble detection routine is only performed on devices of a particular predetermined size, for example excluding tablets or other devices having screens larger than some predetermined threshold (e.g., greater than 5" screen, greater than 6", greater than 7", etc.). In other embodiments, the bubble detection routine can be applied to devices of all sizes.

Next, the bubble detection routine can blur each slice and calculate the average brightness and the standard deviation of brightness for each slice. Blurring the image can prevent the bubble detector from inappropriately labeling thin cracks as bubbles. For each blurred slice, the routine then can compute the ratio of disproportionally bright pixels to total pixels in that slice. Here, "disproportionally bright pixels" can be defined as any pixels that exceed the average brightness of the blurred slice by a predetermined amount, for example more than 5% above the average brightness of the blurred slice, more than 30% above the average brightness of the blurred slice, etc. The ratio of such disproportionally bright pixels to the total pixels in a given blurred slice is calculated. For each individual slice, a bubble is indicated if (1) the ratio of disproportionally bright pixels to total pixels in the blurred slice exceeds some threshold (e.g., greater than 2), and (2) if the standard deviation falls within a predetermined range (e.g., more than 4 and less than 40). This first criteria indicates that there is a bubble-like brightness in the slice and the second criteria excludes those slices in which artifacts may be skewing the results, for example the glass is too smooth indicating an anomalous image or there are genuine cracks or a plurality of slits that skew the result. In some embodiments, only one or the other of these two criteria are used to determine if a bubble is indicated. For example, if the ratio of disproportionally bright pixels to total pixels in the blurred slice exceeds some threshold, then a bubble is indicated in the slice. Separately, if the standard deviation falls within a predetermined range (e.g., more than 4 and less than 40), then a bubble is indicated in the slice.

In decision block 219, the routine determines whether the identified bubbles exceed a predetermined threshold. For example, the routine 200 can assess whether the number of slices with bubbles that were identified, if any, in block 217 exceeds a predetermined threshold (e.g., greater than 3 slices). If so, the routine 200 can proceed to block 211 to indicate the presence of a screen cover. If the routine 200 determines that the number of bubbles identified in block 217 falls below a predetermined threshold, then the routine 200 ends.

If the routine 200 proceeds with evaluating an electronic device screen and finds that the vertical and/or horizontal line segments do not exceed the predetermined threshold, that the corner line segments do not exceed the predetermined threshold, and that there are no identified bubbles, then either there is no screen cover present, or if there is a screen cover present, it is unlikely to be contributing a large number of false positive cracks identified by the line segment detection algorithm. If there is no screen cover present, then a device evaluation process can continue with evaluating the condition of the device screen. Similarly, if there is a screen cover present but it has produced few or no false cracks, then a device evaluation process can continue with evaluating the condition of the device screen without artifacts attributable to a screen cover skewing the evaluation.

Figure 3:
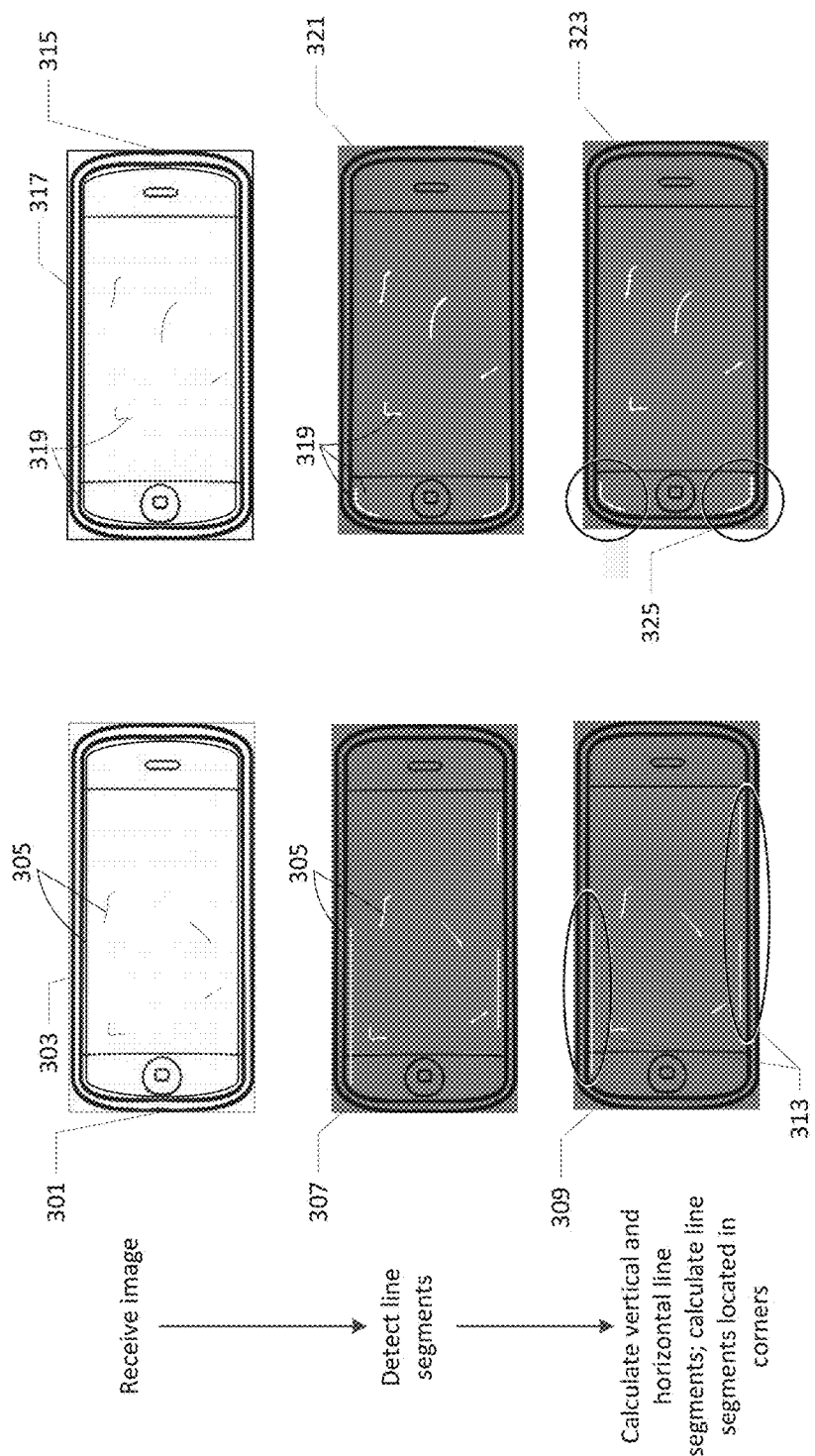
FIG. 3 is a flow diagram of selected operations in the method shown in FIG. 2 along with corresponding images of electronic devices.

FIG. 3 illustrates example images of mobile devices at various stages of the routine illustrated in FIG. 2. Image 301 is an image of a first electronic device screen 303 with a screen cover. The screen 303 includes plurality of cracks or crack-like artifacts 305 (e.g., a line resulting from the outer edge of a screen cover) as seen in image 301. As described above, the routine 200 automatically detects line segments in the image (as described above with respect to block 203), for example using an edge detector algorithm or other suitable crack-detection algorithm. The output of the edge detector is shown in image 307, in which line segments 305 have been identified. Next, vertical and horizontal line segments are calculated (as described above with respect to blocks 205 and 207), and line segments in corner regions are calculated (as described above with respect to block 213). Image 309 shows the identified line segments 313 which are horizontally aligned. In this instance, the primarily horizontal line segments 313 constitute the majority of line segments on the screen 303. Accordingly, the horizontal line segments exceed the predetermined threshold (as described above with respect to block 209), and the presence of a screen cover is indicated.

Image 315 is an image of a second electronic screen 317 device with a screen cover. The screen 317 includes a plurality of cracks or crack-like artifacts 319 (e.g., a line resulting from the outer edge of a screen cover). Image 321 shows the output of the edge detector algorithm applied to the first image 315 (as described above with respect to block 203), in which line segments 319 have been identified. Image 323 shows the identified line segments 325 that are confined to the corner regions of the electronic device (as described above with respect to block 213). In this case, the corner line segments 325 exceed the predetermined threshold (as described above with respect to block 213), so the presence of a screen cover is indicated.

In at least some embodiments, the routine further assesses a condition of the electronic device after determining the presence or absence of a screen cover, such as to evaluate lines detected in the image other than lines associated with a screen cover. For example, to determine whether the screen is cracked, the routine can determine an amount of the identified line segments that are not determined to be horizontal, vertical, or corner line segments. These line segments are more likely to correspond to actual cracks in the screen and accordingly can be counted or otherwise used to evaluate the condition of the screen. In some embodiments, more weight is given to such line segments that are farther from the perimeter of the device (i.e., nearer to a center of the screen) than to those line segments that are closer to the perimeter of the device (i.e., farther from the center of the device screen). In another embodiment, determining whether the screen is cracked includes determining which line segments of the identified line segments are not horizontal, vertical, or corner line segments, and giving more weight to such line segments that are farther from being vertical or horizontal than to such line segments that are nearer to being vertical or horizontal.

Computing Environment

Referring again to FIG. 1, additional details are set forth below regarding the computing environment in which the routine 200 can be performed. The imaging device 101 can be, for example, a digital camera (e.g., having a CCD or CMOS sensor) capable of capturing still and/or moving images of the electronic device 103, and transmitting captured images over the communications link 109 to remote devices. The imaging device 101 can include a camera and an associated fixture, base, or other imaging area in which the electronic device 103 is to be placed for imaging. This can provide a standard background against which the images and/or video of the electronic device 103 are obtained. The imaging device 101 can be configured to move the camera and/or the associated optics in order to capture images and/or video of the electronic device 103 from various angles. The imaging device 101 can also include an illumination source (e.g., LEDs, fluorescent bulbs, lamps, etc.) which can also aid in obtaining images of the electronic device 103 under uniform lighting conditions.

The electronic device 103 can be, for example, a smartphone, a tablet, a laptop, a handheld gaming device, a media player, or any such device that has a screen or other surface that may suffer cracks or similar defects. Although many embodiments of the present technology are described herein in the context of mobile phones, aspects of the present technology are not limited to mobile phones and generally apply to other consumer electronic devices. Such devices include, as non-limiting examples, all manner of mobile phones; smartphones; handheld devices; personal digital assistants (PDAs); MP3 or other digital music players; tablet, notebook, ultrabook and laptop computers; e-readers; all types of cameras; GPS devices; set-top boxes and other media players; VoIP phones; universal remote controls; wearable computers; and larger consumer electronic devices, such as desktop computers, TVs, projectors, DVRs, game consoles, etc.

The computing device 105 can be a desktop computer or another suitable device. The computing device 105 is configured to receive images of the electronic device 103 from the imaging device 101 and to automatically analyze the images to detect the presence of screen covers as well as cracks or other defects. In some embodiments, the computing device 105 is remote from the imaging device 101 and can be in communication via the communications link 109. In other embodiments, the computing device 105 is connected to the imaging device 101 via a hardwire connection, or in certain embodiments the imaging device 101 and the computing device 105 are integrated into the same machine. The computing device 105 is also in communication with the database 107 which can store data used in automatically analyzing the images of the electronic device 103. The database 107 may also store the results of the automatic analysis of the images, other data about the electronic device 103, etc.

In the illustrated embodiment, various devices including the imaging device 101 and the computing device 105 exchanges information with one another via the communication link 109. Although the communication link 109 can include a publicly available network (e.g., the Internet with a web interface), a private communication link (e.g., an intranet or other network) can also be used. Moreover, in various embodiments the imaging device 101 is connected to a host computer (not shown) that facilitates the exchange of information between the imaging device 101, the computing device 105, remote computers, mobile devices, etc.

In the illustrated embodiment, the imaging device 101 includes the processing component 111 that controls operation of the imaging device 101 in accordance with computer-readable instructions stored in memory 113. The processing component 111 may include any logic processing unit, such as one or more central processing units (CPUs), graphics processing units (GPUs), digital signal processors (DSPs), application-specific integrated circuits (ASICs), etc. The processing component 111 may be a single processing unit or multiple processing units in an electronic device or distributed across multiple devices. Aspects of the present technology can be embodied in a special purpose computing device or data processor that is specifically programmed, configured, or constructed to perform one or more of the computer-executable instructions explained in detail herein. Aspects of the present technology can also be practiced in distributed computing environments in which functions or modules are performed by remote processing devices that are linked through a communications network, such as a local area network (LAN), wide area network (WAN), or the Internet. In a distributed computing environment, modules can be located in both local and remote memory storage devices.

The processing component 111 is connected to memory 113, which can include a combination of temporary and/or permanent storage, and both read-only memory (ROM) and writable memory (e.g., random access memory or RAM), writable non-volatile memory such as flash memory or other solid-state memory, hard drives, removable media, magnetically or optically readable discs, nanotechnology memory, biological memory, and so forth. As used herein, memory does not include a transitory propagating signal per se. The memory 213 includes data storage that contains programs, software, and information, such as an operating system and data. Imaging device 101 operating system and data can include software and databases configured to control imaging device 101 components, process images, communicate and exchange data and information with remote computers and other devices, etc.

The imaging device 101 further includes input components 115 that can receive input from user interactions and provide input to the processing component 111, typically mediated by a hardware controller that interprets the raw signals received from the input device and communicates the information to the processing component 111 using a known communication protocol. Examples of an input component 115 include touchpad, a keyboard (with physical or virtual keys), a pointing device (such as a mouse, dial, or eye tracking device), a touchscreen that detects contact events when it is touched by a user, a microphone that receives audio input, etc. The imaging device 101 can also include various other input components 115 such as GPS or other location determination sensors, motion sensors, wearable input devices with accelerometers (e.g. wearable glove-type input devices), biometric sensors (e.g., fingerprint sensors), light sensors, card readers (e.g., magnetic stripe readers or memory card readers) or the like.

The processing component 111 is also connected to one or more various output components 117, e.g., directly or via a hardware controller. The output devices can include a display on which text and graphics are displayed. The display can be, for example, an LCD, LED, or OLED display screen, an e-ink display, a projected display (such as a heads-up display device), and/or a display integrated with a touchscreen that serves as an input device as well as an output device that provides graphical and textual visual feedback to a user. The output components 117 can also include a speaker for playing audio signals, haptic feedback devices for tactile output such as vibration, etc. In some implementations, a speaker and microphone are implemented by a combined audio input-output device.

In the illustrated embodiment, the imaging device 101 further includes one or more communication components 119. The communication components can include, for example, a wireless transceiver 121 (e.g., one or more of a Wi-Fi transceiver; Bluetooth transceiver; near-field communication (NFC) device; wireless modem or cellular radio utilizing GSM, CDMA, 3G and/or 4G technologies; etc.) and/or a wired network connection 123 (e.g., one or more of an Ethernet port, cable modem, FireWire cable, Lightning connector, universal serial bus (USB) port, etc.). The communication components 119 are suitable for communication between the imaging device 101 and other local and/or remote devices, e.g., the computing device 105, directly via a wired or wireless peer-to-peer connection and/or indirectly via the communication link 109 (which can include the Internet, a public or private intranet, a local or extended Wi-Fi network, cell towers, the plain old telephone system (POTS), etc.). For example, the wireless transceiver 121 of the imaging device 101 can connect to a wireless transceiver 149 of the computing device via the wireless connection. The imaging device 101 further includes power 125, which can include battery power and/or facility power for operation of the various electrical components associated with the imaging device 101.

The imaging device 101 further includes the image sensor 127, optics 129, and illumination source 131. The image sensor 127 can be, for example, a CCD sensor, a CMOS sensor, or any other type of image sensor or array of sensors. The image sensor 127 can be aligned with optics 129, for example one or more lenses, filters, or other optical elements, configured to orient and modulate incoming light before it reaches the image sensor 127. The illumination source 131 can be configured to direct illumination towards the field of view of the imaging device 101, and can be any type of light source, for example LEDs, fluorescent bulbs, etc. In some embodiments, the illumination source 131 includes multiple different types of light sources which can be individually activated, for example infrared, ultraviolet, broadband, etc.

The computing device 105 includes several components similar to those in the imaging device 101. In the illustrated embodiment, the computing device 105 includes a processing component 133 that controls operation of the computing device 105 in accordance with computer-readable instructions stored in memory 135. The processing component 133 may be any logic processing unit, such as one or more central processing units (CPUs), graphics processing units (GPUs), digital signal processors (DSPs), application-specific integrated circuits (ASICs), etc. The processing component 133 may be a single processing unit or multiple processing units in an electronic device or distributed across multiple devices. The processing component 133 is connected to memory 135, which includes data storage that contains programs, software, and information, such as an operating system 137, application programs 139, and data 141. The operating system 137 can include, for example, Windows®, Linux®, Android™, iOS®, and/or an embedded real-time operating system. The application programs 139 and data 141 can include software and databases configured to control computing device 105 components, process and evaluate images received from the imaging device 101, communicate and exchange data and information with remote computers and other devices, etc.

The computing device 105 can include input components 143, such as a keyboard (with physical or virtual keys), a pointing device (such as a mouse, joystick, dial, or eye tracking device), a touchscreen, a microphone, and a camera for still photograph and/or video capture. The computing device 105 can also include various other input components 143 such as GPS or other location determination sensors, motion sensors, wearable input devices with accelerometers (e.g. wearable glove-type input devices), biometric sensors (e.g., fingerprint sensors), light sensors, card readers (e.g., magnetic stripe readers or memory card readers) and the like.

The processing component 133 can also be connected to one or more various output components 145, e.g., directly or via a hardware controller. The output devices can include a display such as an LCD, LED, or OLED display screen (such as a desktop computer screen, handheld device screen, or television screen), an e-ink display, a projected display (such as a heads-up display device), and/or a display integrated with a touchscreen that serves as an input device as well as an output device that provides graphical and textual visual feedback to the user. The output devices can also include a speaker for playing audio signals, haptic feedback devices for tactile output such as vibration, etc.

In the illustrated embodiment, computing device 105 further includes one or more communication components 147. The communication components can include, for example, a wireless transceiver 149 (e.g., one or more of a Wi-Fi transceiver; Bluetooth transceiver; near-field communication (NFC) device; wireless modem or cellular radio utilizing GSM, CDMA, 3G and/or 4G technologies; etc.) and/or a wired network connector port 251 (e.g., one or more of an Ethernet port, cable modem, FireWire cable, Lightning connector, universal serial bus (USB) port, etc.). The communication components 147 are suitable for communication between the computing device 105 and other local and/or remote computing devices, e.g., the imaging device 101 via a wired or wireless peer-to-peer connection and/or indirectly via the communication link 109. For example, the wireless transceiver 149 of the computing device 105 can connect to the wireless transceiver 121 of imaging device 101, and/or the wired connector port 151 of the computing device 105 can connect to the wired connector port 123 of the imaging device 101. The computing device 105 further includes power 153, which can include battery power and/or facility power for operation of the various electrical components associated with the computing device 105.

Unless described otherwise, the construction and operation of the various components shown in FIG. 1 are of conventional design. As a result, such components need not be described in further detail herein, as they will be readily understood by those skilled in the relevant art. In other embodiments, the computing device 105 and the imaging device 101 include other features that may be different from those described above. In still further embodiments, the computing device 105 and/or the imaging device 101 include more or fewer features similar to those described above.

Kiosk Environment

Figure 4:
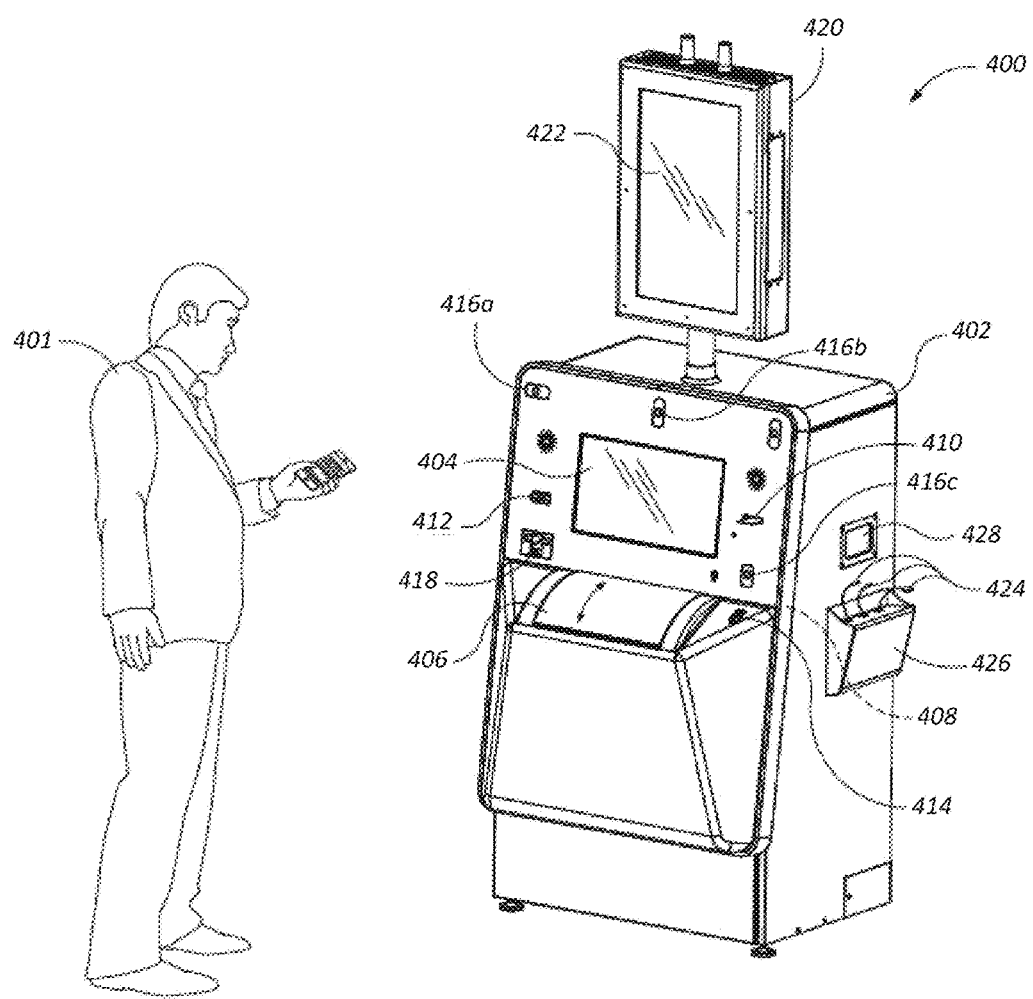
FIG. 4 is an isometric view of a machine employing methods and systems in accordance embodiments of the present technology for recycling mobile phones and/or other electronic devices.

In some embodiments, the routines described herein can be carried out using a kiosk that includes an imaging device (e.g., the imaging device 101) therein. In some embodiments, the kiosk can perform some or all of the functions performed by the computing device 105 described above, for example processing and evaluating images received from the imaging device 101. The kiosk can include, for example, a processing component and memory storing instructions that, when executed by the processing component, perform operations such as the routine 200 described above. FIG. 4, for example, is an isometric view of a kiosk 400 for recycling and/or other processing of mobile phones and other consumer electronic devices in accordance with the present technology. The term "processing" is used herein for ease of reference to generally refer to all manner of services and operations that may be performed or facilitated by the kiosk 400 on, with, or otherwise in relation to an electronic device. Such services and operations can include, for example, selling, reselling, recycling, donating, exchanging, identifying, evaluating, pricing, auctioning, decommissioning, transferring data from or to, reconfiguring, refurbishing, etc., mobile phones and other electronic devices. Although many embodiments of the present technology are described herein in the context of mobile phones, aspects of the present technology are not limited to mobile phones and generally apply to other consumer electronic devices. Such devices include, as non-limiting examples, all manner of mobile phones, smart phones, handheld devices, PDAs, MP3 players, tablet, notebook and laptop computers, e-readers, cameras, etc. In some embodiments, it is contemplated that the kiosk 400 can facilitate selling and/or otherwise processing larger consumer electronic devices, such as desktop computers, TVs, game consoles, etc., as well smaller electronic devices such as Google Glass™, smart-watches, etc.

In the illustrated embodiment, the kiosk 400 is a floor-standing self-service kiosk configured for use by a user 401 (e.g., a consumer, customer, etc.) to recycle, sell, and/or perform other operations with a mobile phone or other consumer electronic device. In other embodiments, the kiosk 400 can be configured for use on a countertop or a similar raised surface. Although the kiosk 400 is configured for use by consumers, in various embodiments the kiosk 400 and/or various portions thereof can also be used by other operators, such as a retail clerk or kiosk assistant to facilitate the selling or other processing of mobile phones and other electronic devices.

In the illustrated embodiment, the kiosk 400 includes a housing 402 that is approximately the size of a conventional vending machine. The housing 402 can be of conventional manufacture from, for example, sheet metal, plastic panels, etc. A plurality of user interface devices are provided on a front portion of the housing 402 for providing instructions and other information to users, and/or for receiving user inputs and other information from users. For example, the kiosk 400 can include a display screen 404 (e.g., a liquid crystal display ("LCD") or light emitting diode ("LED") display screen, a projected display (such as a heads-up display or a head-mounted device), and so on) for providing information, prompts, etc., to users. The display screen 404 can include a touch screen for receiving user input and responses to displayed prompts. In addition or alternatively, the kiosk 400 can include a separate keyboard or keypad for this purpose. The kiosk 400 can also include an ID reader or scanner 412 (e.g., a driver's license scanner), a fingerprint reader 414, and one or more cameras 416 (e.g., digital still and/or video cameras, identified individually as cameras 416*a-c*). The kiosk 400 can additionally include output devices such as a label printer having an outlet 410, and a cash dispenser having an outlet 418. Although not identified in FIG. 4, the kiosk 400 can further include a speaker and/or a headphone jack for audibly communicating information to users, one or more lights for visually communicating signals or other information to users, a handset or microphone for receiving verbal input from the user, a card reader (e.g., a credit/debit card reader, loyalty card reader, etc.), a receipt or voucher printer and dispenser, as well as other user input and output devices. The input devices can include a touch-pad, pointing device such as a mouse, joystick, pen, game pad, motion sensor, scanner, eye direction monitoring system, etc. Additionally the kiosk 400 can also include a bar code reader, QR code reader, bag/package dispenser, a digital signature pad, etc. In the illustrated embodiment, the kiosk 400 additionally includes a header 420 having a display screen 422 for displaying marketing advertisements and/or other video or graphical information to attract users to the kiosk. In addition to the user interface devices described above, the front portion of the housing 402 also includes an access panel or door 406 located directly beneath the display screen 404. As described in greater detail below, the access door is configured to automatically retract so that the user 401 can place an electronic device (e.g., a mobile phone) in an inspection area 408 for automatic inspection by the kiosk 400.

A sidewall portion of the housing 402 can include a number of conveniences to help users recycle or otherwise process their mobile phones. For example, in the illustrated embodiment the kiosk 400 includes an accessory bin 428 that is configured to receive mobile device accessories that the user wishes to recycle or otherwise dispose of. Additionally, the kiosk 400 can provide a free charging station 426 with a plurality of electrical connectors 424 for charging a wide variety of mobile phones and other consumer electronic devices.

Figure 5B:
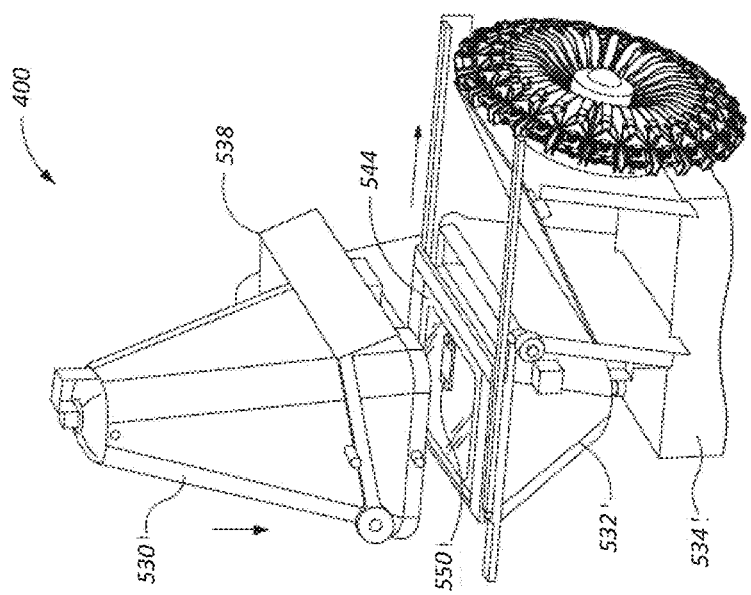
FIGS. 5A-5D are a series of isometric views of the machine of FIG. 4 with a number of exterior panels removed to illustrate operation of the machine in accordance with an embodiment of the present technology.
Figure 5A:
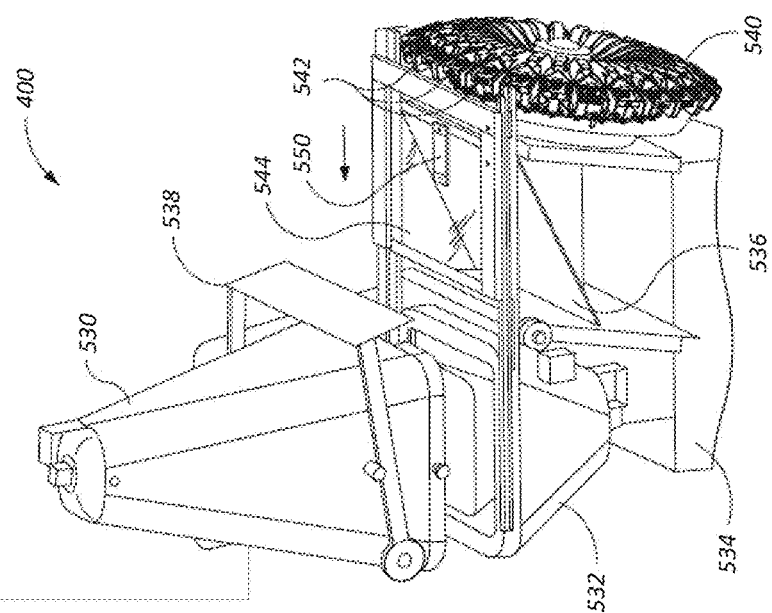

FIGS. 5A-5D are a series of isometric views of the kiosk 400 with the housing 402 removed to illustrate selected internal components configured in accordance with an embodiment of the present technology. Referring first to FIG. 5A, in the illustrated embodiment the kiosk 400 includes a connector carrier 540 and an inspection plate 544 operably disposed behind the access door 406 (FIG. 4). In the illustrated embodiment, the connector carrier 540 is a rotatable carrousel that is configured to rotate about a generally horizontal axis and carries a plurality of electrical connectors 542 (e.g., approximately 25 connectors) distributed around an outer periphery thereof. In other embodiments, other types of connector carrying devices (including both fixed and movable arrangements) can be used. In some embodiments, the connectors 542 includes a plurality of interchangeable USB connectors configured to provide power and/or exchange data with a variety of different mobile phones and/or other electronic devices. In operation, the connector carrier 540 is configured to automatically rotate about its axis to position an appropriate one of the connectors 542 adjacent to an electronic device, such as a mobile phone 550, that has been placed on the inspection plate 544 for recycling. The connector 542 can then be manually and/or automatically withdrawn from the connector carrier 540 and connected to a port on the mobile phone 550 for electrical analysis. Such analysis can include, e.g., an evaluation of the make, model, configuration, condition, etc.

In the illustrated embodiment, the inspection plate 544 is configured to translate back and forth (on, e.g., parallel mounting tracks) to move an electronic device, such as the mobile phone 550, between a first position directly behind the access door 406 and a second position between an upper chamber 530 and an opposing lower chamber 532. Moreover, in this embodiment the inspection plate 544 is transparent, or at least partially transparent (e.g., formed of glass, Plexiglas, etc.) to enable the mobile phone 550 to be photographed and/or otherwise optically evaluated from all, or at least most viewing angles (e.g., top, bottom, sides, etc.) using, e.g., one or more cameras, mirrors, etc. mounted to or otherwise associated with the upper and lower chambers 530 and 532. When the mobile phone 550 is in the second position, the upper chamber 530 can translate downwardly to generally enclose the mobile phone 550 between the upper chamber 530 and the lower chamber 532. The upper chamber 530 is operably coupled to a gate 538 that moves up and down in unison with the upper chamber 530.

In some embodiments, the kiosk 400 includes the imaging device 101 disposed within the upper hood 530. The imaging device 101 can be used as described above to facilitate visual inspection of the mobile phone 550 in order to detect the presence of a screen cover over the screen, and depending on that determination, proceeding to evaluate the screen for cracks. The upper chamber 530 and/or the lower chamber 532 can also include one or more magnification tools, scanners (e.g., bar code scanners, infrared scanners, etc.) or other imaging components (not shown) and an arrangement of mirrors (also not shown) to view, photograph and/or otherwise visually evaluate the mobile phone 550 from multiple perspectives. In some embodiments, one or more of the cameras and/or other imaging components discussed above can be movable to facilitate device evaluation. For example, as noted above with respect to FIG. 1, the imaging device 101 can be affixed to a moveable mechanical component such as an arm, which in turn can be moved using a belt drive, rack and pinion system, or other suitable drive system coupled to an electronic controller (e.g., the computing device 105). The inspection area 408 can also include weight scales, heat detectors, UV readers/detectors, and the like, for further evaluation of electronic devices placed therein. The kiosk 400 can further include an angled binning plate 536 for directing electronic devices from the transparent plate 544 into a collection bin 534 positioned in a lower portion of the kiosk 400.

The kiosk 400 can be used in a number of different ways to efficiently facilitate the recycling, selling and/or other processing of mobile phones and other consumer electronic devices. Referring to FIGS. 4-5D together, in one embodiment a user wishing to sell a used mobile phone, such as the mobile phone 550, approaches the kiosk 400 and identifies the type of device the user wishes to sell in response to prompts on the display screen 404. Next, the user may be prompted to remove any cases, stickers, or other accessories from the device so that it can be accurately evaluated. Additionally, the kiosk 400 may print and dispense a unique identification label (e.g., a small adhesive-backed sticker with a quick response code ("QR code"), barcode, or other machine-readable indicia, etc.) from the label outlet 410 for the user to adhere to the back of the mobile phone 550. After this is done, the door 406 retracts and opens allowing the user to place the mobile phone 550 onto the transparent plate 544 in the inspection area 408 (FIG. 5A). The door 406 then closes and the transparent plate 544 moves the mobile phone 550 under the upper chamber 530 as shown in FIG. 5B. The upper chamber 530 then moves downwardly to generally enclose the mobile phone 550 between the upper and lower chambers 530 and 532, and the cameras and/or other imaging components in the upper and lower chambers 530 and 532 perform a visual inspection of the mobile phone 550. In one embodiment, the visual inspection of the mobile phone 550 includes performing the routine 200 (FIG. 2) to detect a screen cover over the screen. In some embodiments, the visual inspection includes a computer-implemented visual analysis (e.g., a three-dimensional ("3D") analysis) performed by a processing device within the kiosk (e.g., a CPU) to confirm the identification of the mobile phone 550 (e.g. make, model and/or sub-model) and/or to evaluate or assess the condition and/or function of the mobile phone 550 and/or its various components and systems. For example, the visual analysis can include computer-implemented evaluation (e.g., a digital comparison) of images of the mobile phone 550 taken from top, side and/or end view perspectives to determine length, width, and/or height (thickness) dimensions of the mobile phone 550. The visual analysis can further include a computer-implemented inspection of a display screen on the mobile phone 550 to check for, e.g., cracks in the glass and/or other damage or defects in the LCD (e.g., defective pixels, etc.).

Figure 5C:
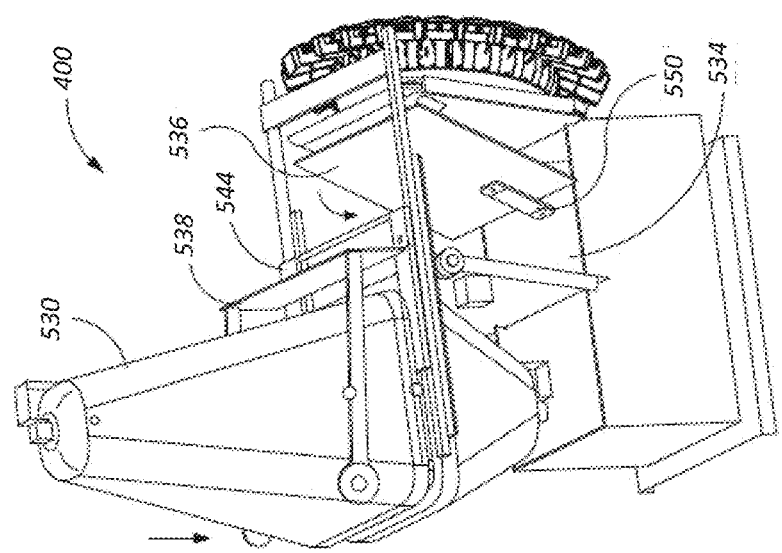
Figure 5D:
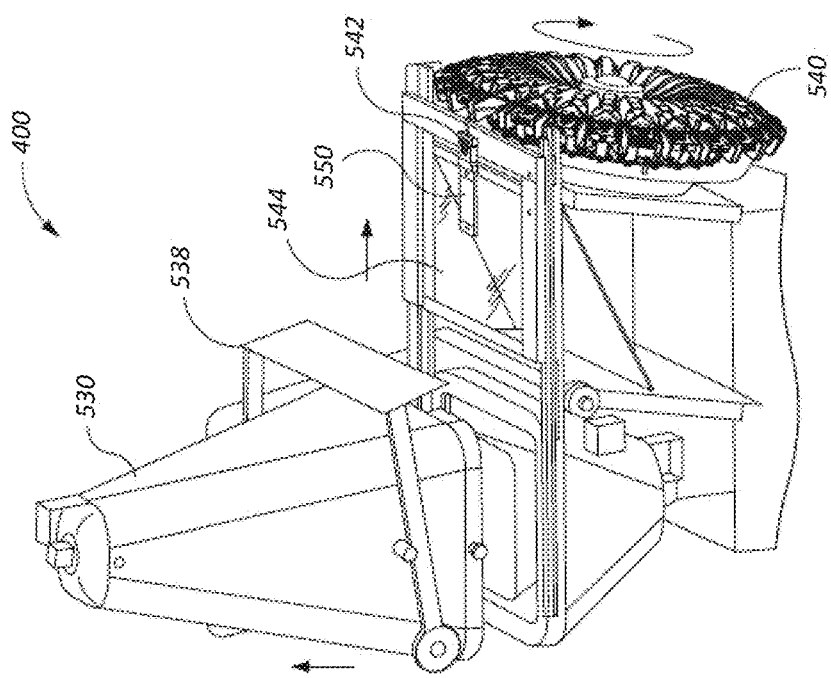

Referring next to FIG. 5C, after the visual analysis is performed and the device has been identified, the upper chamber 530 returns to its upper position and the transparent plate 544 returns the mobile phone 550 to its initial position near the door 406. The display screen 404 can also provide an estimated price, or an estimated range of prices, that the kiosk 400 may offer the user for the mobile phone 550 based on the visual analysis, and/or based on user input (e.g., input regarding the type, condition, etc. of the phone 550). If the user indicates (via, e.g., input via the touch screen) that they wish to proceed with the transaction, the connector carrier 540 automatically rotates an appropriate one of the connectors 542 into position adjacent the transparent plate 544, and door 406 is again opened. The user can then be instructed (via, e.g., the display screen 404) to withdraw the selected connector 542 (and its associated wire) from the carrousel 540, plug the connector 542 into the corresponding port (e.g., a USB port) on the mobile phone 550, and reposition the mobile phone 550 in the inspection area on the transparent plate 544. After doing so, the door 406 once again closes and the kiosk 400 (e.g. the kiosk CPU) performs an electrical inspection of the device via the connector 542 to further evaluate the condition of the phone as well as specific component and operating parameters such as the memory, carrier, etc. In addition or alternatively, in some embodiments the electrical inspection can include a determination of phone manufacturer information (e.g., a vendor identification number or VID) and product information (e.g., a product identification number or PID). In some embodiments, the kiosk 400 can perform the electrical analysis using one or more of the methods and/or systems described in detail in the commonly owned patents and patent applications identified herein and incorporated by reference in their entireties.

After the visual and electronic analysis of the mobile phone 550, the user is presented with a phone purchase price via the display screen 404. If the user declines the price (via, e.g., the touch screen), a retraction mechanism (not shown) automatically disconnects the connector 542 from the mobile phone 550, the door 406 opens, and the user can reach in and retrieve the mobile phone 550. If the user accepts the price, the door 406 remains closed and the user may be prompted to place his or her identification (e.g., a driver's license) in the ID scanner 412 and provide a thumbprint via the fingerprint reader 414. As a fraud prevention measure, the kiosk 400 can be configured to transmit an image of the driver's license to a remote computer screen, and an operator at the remote computer can visually compare the picture (and/or other information) on the driver's license to an image of the person standing in front of the kiosk 400 as viewed by one or more of the cameras 416a-c (FIG. 4) to confirm that the person attempting to sell the phone 550 is in fact the person identified by the driver's license. In some embodiments, one or more of the cameras 416a-c can be movable to facilitate viewing of kiosk users, as well as other individuals in the proximity of the kiosk 400. Additionally, the person's fingerprint can be checked against records of known fraud perpetrators. If either of these checks indicate that the person selling the phone presents a fraud risk, the transaction can be declined and the mobile phone 550 returned. After the user's identity has been verified, the transparent plate 544 moves back toward the upper and lower chambers 530 and 532. As shown in FIG. 5D, however, when the upper chamber 530 is in the lower position the gate 538 permits the transparent plate 544 to slide underneath but not electronic devices carried thereon. As a result, the gate 538 knocks the mobile phone 550 off of the transparent plate 544, onto the binning plate 536 and into the bin 534. The kiosk can then provide payment of the purchase price to the user. In some embodiments, payment can be made in the form of cash dispensed from the cash outlet 418. In other embodiments, the user can receive remuneration for the mobile phone 550 in various other useful ways. For example, the user can be paid via a redeemable cash voucher, a coupon, an e-certificate, a prepaid card, a wired or wireless monetary deposit to an electronic account (e.g., a bank account, credit account, loyalty account, online commerce account, mobile wallet etc.), Bitcoin, etc.

As those of ordinary skill in the art will appreciate, the foregoing routines are but some examples of ways in which the kiosk 400 can be used to recycle or otherwise process consumer electronic devices such as mobile phones. Although the foregoing example is described in the context of mobile phones, it should be understood that the kiosk 400 and various embodiments thereof can also be used in a similar manner for recycling virtually any consumer electronic device, such as MP3 players, tablet computers, PDAs, and other portable devices, as well as other relatively non-portable electronic devices such as desktop computers, printers, devices for implementing games, entertainment or other digital media on CDs, DVDs, Blu-ray, etc. Moreover, although the foregoing example is described in the context of use by a consumer, the kiosk 400 in various embodiments thereof can similarly be used by others, such as a store clerk, to assist consumers in recycling, selling, exchanging, etc. their electronic devices.

The disclosed technology also includes the disclosures of U.S. patent application Ser. No. 14/498,763, titled "METHODS AND SYSTEMS FOR PRICING AND PERFORMING OTHER PROCESSES ASSOCIATED WITH RECYCLING MOBILE PHONES AND OTHER ELECTRONIC DEVICES," filed by the applicant on Sep. 26, 2014; U.S. patent application Ser. No. 14/500,739, titled "MAINTAINING SETS OF CABLE COMPONENTS USED FOR WIRED ANALYSIS, CHARGING, OR OTHER INTERACTION WITH PORTABLE ELECTRONIC DEVICES," filed by the applicant on Sep. 29, 2014; U.S. patent application Ser. No. 14/873,158, titled "WIRELESS-ENABLED KIOSK FOR RECYCLING CONSUMER DEVICES," filed by the applicant on Oct. 1, 2015; U.S. patent application Ser. No. 14/873,145, titled "APPLICATION FOR DEVICE EVALUATION AND OTHER PROCESSES ASSOCIATED WITH DEVICE RECYCLING," filed by the applicant on Oct. 1, 2015; U.S. patent application Ser. No. 14/506,449, titled "SYSTEM FOR ELECTRICALLY TESTING MOBILE DEVICES AT A CONSUMER-OPERATED KIOSK, AND ASSOCIATED DEVICES AND METHODS," filed by the applicant on Oct. 3, 2014; U.S. patent application Ser. No. 14/925,357, titled "SYSTEMS AND METHODS FOR RECYCLING CONSUMER ELECTRONIC DEVICES," filed by the applicant on Oct. 28, 2015; U.S. patent application Ser. No. 14/925,375, titled "METHODS AND SYSTEMS FOR FACILITATING PROCESSES ASSOCIATED WITH INSURANCE SERVICES AND/OR OTHER SERVICES FOR ELECTRONIC DEVICES," filed by the applicant on Oct. 28, 2015; U.S. patent application Ser. No. 14/964,963, titled "METHODS AND SYSTEMS FOR PROVIDING INFORMATION REGARDING COUPONS/PROMOTIONS AT KIOSKS FOR RECYCLING MOBILE PHONES AND OTHER ELECTRONIC DEVICES," filed by the applicant on Dec. 10, 2015; U.S. patent application Ser. No. 14/568,051, titled "METHODS AND SYSTEMS FOR IDENTIFYING MOBILE PHONES AND OTHER ELECTRONIC DEVICES," filed by the applicant on Dec. 11, 2014; U.S. patent application Ser. No. 14/966,346, titled "SYSTEMS AND METHODS FOR RECYCLING CONSUMER ELECTRONIC DEVICES," filed by the applicant on Dec. 11, 2015; U.S. patent application Ser. No. 14/598,469, titled "METHODS AND SYSTEMS FOR DYNAMIC PRICING AND PERFORMING OTHER PROCESSES ASSOCIATED WITH RECYCLING MOBILE PHONES AND OTHER ELECTRONIC DEVICES," filed by the applicant on Jan. 16, 2015; U.S. patent application Ser. No. 14/660,768, titled "SYSTEMS AND METHODS FOR INSPECTING MOBILE DEVICES AND OTHER CONSUMER ELECTRONIC DEVICES WITH A LASER," filed by the applicant on Mar. 17, 2015; U.S. patent application Ser. No. 14/663,331, titled "DEVICE RECYCLING SYSTEMS WITH FACIAL RECOGNITION," filed by the applicant on Mar. 19, 2015; U.S. provisional application No. 62/169,072, titled "METHODS AND SYSTEMS FOR VISUALLY EVALUATING ELECTRONIC DEVICES," filed by the applicant on Jun. 1, 2015; U.S. provisional application No. 62/202,330, titled "METHODS AND SYSTEMS FOR INSPECTING MOBILE DEVICES AND OTHER CONSUMER ELECTRONIC DEVICES WITH ROBOTIC ACTUATION," filed by the applicant on Aug. 7, 2015; U.S. patent application Ser. No. 15/057,707, titled "METHODS AND SYSTEMS FOR RECORDING INTERACTIONS WITH A SYSTEM FOR PURCHASING MOBILE PHONES AND OTHER ELECTRONIC DEVICES," filed by the applicant on Mar. 1, 2016; U.S. patent application Ser. No. 14/873,158, titled "WIRELESS-ENABLED KIOSK FOR RECYCLING CONSUMER DEVICES," filed by the applicant on Oct. 1, 2015; U.S. patent application Ser. No. 14/873,145, titled "APPLICATION FOR DEVICE EVALUATION AND OTHER PROCESSES ASSOCIATED WITH DEVICE RECYCLING," filed by the applicant on Oct. 1, 2015; U.S. patent application Ser. No. 14/925,357 titled "SYSTEMS AND METHODS FOR RECYCLING CONSUMER ELECTRONIC DEVICES," filed by the applicant on Oct. 28, 2015; U.S. patent application Ser. No. 14/925,375, titled "METHODS AND SYSTEMS FOR FACILITATING PROCESSES ASSOCIATED WITH INSURANCE SERVICES AND/OR OTHER SERVICES FOR ELECTRONIC DEVICES," filed by the applicant on Oct. 28, 2015; U.S. patent application Ser. No. 14/934,134, titled "METHODS AND SYSTEMS FOR EVALUATING AND RECYCLING ELECTRONIC DEVICES," and U.S. patent application Ser. No. 14/967,183, titled "SYSTEMS AND METHODS FOR RECYCLING CONSUMER ELECTRONIC DEVICES," filed Dec. 11, 2015, each of which is incorporated herein by reference in its entirety. All of the patents and patent applications listed above are commonly owned by the applicant of the present application, and they along with any other patents or patent applications identified herein are incorporated herein by reference in their entireties.

While the Internet is shown, a private network, such as an intranet may likewise be used herein. The network may have a client-server architecture, in which a computer is dedicated to serving other client computers, or it may have other architectures such as peer-to-peer, in which one or more computers serve simultaneously as servers and clients. A database or databases, coupled to the server computer(s), stores much of the web pages and content exchanged between the user computers. The server computer(s), including the database(s), may employ security measures to inhibit malicious attacks on the system and preserve the integrity of the messages and data stored therein (e.g., firewall systems, message encryption and/or authentication (e.g., using transport layer security (TLS) or secure socket layers (SSL)), password protection schemes, encryption of stored data (e.g., using trusted computing hardware), and the like).

One skilled in the relevant art will appreciate that the concepts of the invention can be used in various environments other than location based or the Internet. In general, a display description may be in HTML, XML or WAP format, email format or any other format suitable for displaying information (including character/code-based formats, algorithm-based formats (e.g., vector generated), and bitmapped formats). Also, various communication channels, such as local area networks, wide area networks, or point-to-point dial-up connections, may be used instead of the Internet. The system may be conducted within a single computer environment, rather than a client/server environment. Also, the user computers may comprise any combination of hardware or software that interacts with the server computer, such as television-based systems and various other consumer products through which commercial or noncommercial transactions can be conducted. The various aspects of the invention described herein can be implemented in or for any e-mail environment.

Although not required, aspects of the invention are described in the general context of computer-executable instructions, such as routines executed by a general-purpose data processing device, e.g., a server computer, wireless device or personal computer. Those skilled in the relevant art will appreciate that aspects of the invention can be practiced with other communications, data processing, or computer system configurations, including Internet appliances, handheld devices (including personal digital assistants (PDAs)), wearable computers, all manner of cellular or mobile phones (including Voice over IP (VoIP) phones), dumb terminals, media players, gaming devices, multi-processor systems, microprocessor-based or programmable consumer electronics, set-top boxes, network PCs, mini-computers, mainframe computers, and the like. Indeed, the terms "computer," "server," "host," "host system," and the like, are generally used interchangeably herein, and refer to any of the above devices and systems, as well as any data processor. Input devices may include a touchpad, keyboard and/or a pointing device such as a mouse. Other input devices are possible such as a microphone, joystick, pen, game pad, scanner, digital camera, video camera, and the like. The data storage devices may include any type of computer-readable media that can store data accessible by a computer, such as magnetic hard and floppy disk drives, optical disk drives, magnetic cassettes, tape drives, flash memory cards, digital video disks (DVDs), Bernoulli cartridges, RAMs, ROMs, smart cards, etc. Indeed, any medium for storing or transmitting computer-readable instructions and data may be employed, including a connection port to a network such as a local area network (LAN), wide area network (WAN) or the Internet.

Aspects of the invention can be embodied in a special purpose computer or data processor that is specifically programmed, configured, or constructed to perform one or more of the computer-executable instructions explained in detail herein. While aspects of the invention, such as certain functions, are described as being performed exclusively on a single device, the invention can also be practiced in distributed environments where functions or modules are shared among disparate processing devices, which are linked through a communications network, such as a Local Area Network (LAN), Wide Area Network (WAN), or the Internet. In a distributed computing environment, program modules may be located in both local and remote memory storage devices.

Aspects of the invention may be stored or distributed on tangible computer-readable media, including magnetically or optically readable computer discs, hard-wired or preprogrammed chips (e.g., EEPROM semiconductor chips), nanotechnology memory, biological memory, or other data storage media. The data storage devices may include any type of computer-readable media that can store data accessible by a computer, such as magnetic hard and floppy disk drives, optical disk drives, magnetic cassettes, tape drives, flash memory cards, DVDs, Bernoulli cartridges, RAM, ROMs, smart cards, etc. Indeed, any medium for storing or transmitting computer-readable instructions and data may be employed, including a connection port to a network such as a LAN, WAN, or the Internet. Alternatively, computer implemented instructions, data structures, screen displays, and other data under aspects of the invention may be distributed over the Internet or over other networks (including wireless networks), on a propagated signal on a propagation medium (e.g., an electromagnetic wave(s), a sound wave, etc.) over a period of time, or they may be provided on any analog or digital network (packet switched, circuit switched, or other scheme). The terms "memory" and "computer-readable storage medium" include any combination of temporary, persistent, and/or permanent storage, e.g., ROM, writable memory such as RAM, writable non-volatile memory such as flash memory, hard drives, solid state drives, removable media, and so forth, but do not include a propagating signal per se.

The above Detailed Description of examples and embodiments of the invention is not intended to be exhaustive or to limit the invention to the precise form disclosed above. While specific examples for the invention are described above for illustrative purposes, various equivalent modifications are possible within the scope of the invention, as those skilled in the relevant art will recognize. References throughout the foregoing description to features, advantages, or similar language do not imply that all of the features and advantages that may be realized with the present technology should be or are in any single embodiment of the invention. Rather, language referring to the features and advantages is understood to mean that a specific feature, advantage, or characteristic described in connection with an embodiment is included in at least one embodiment of the present technology. Thus, discussion of the features and advantages, and similar language, throughout this specification may, but do not necessarily, refer to the same embodiment. Furthermore, the described features, advantages, and characteristics of the present technology may be combined in any suitable manner in one or more embodiments. One skilled in the relevant art will recognize that the present technology can be practiced without one or more of the specific features or advantages of a particular embodiment. In other instances, additional features and advantages may be recognized in certain embodiments that may not be present in all embodiments of the present technology.

Any patents and applications and other references noted above, including any that may be listed in accompanying filing papers, are incorporated herein by reference. Aspects of the invention can be modified, if necessary, to employ the systems, functions, and concepts of the various references described above to provide yet further implementations of the invention.

Unless the context clearly requires otherwise, throughout the description and the claims, the words "comprise," "comprising," and the like, are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The teachings of the invention provided herein can be applied to other systems, not necessarily the system described above. The elements and acts of the various examples described above can be combined to provide further implementations of the invention. Some alternative implementations of the invention may include not only additional elements to those implementations noted above, but also may include fewer elements. Further any specific numbers noted herein are only examples—alternative implementations may employ differing values or ranges.

While the above description describes various embodiments of the invention and the best mode contemplated, regardless how detailed the above text, the invention can be practiced in many ways. Details of the system may vary considerably in its specific implementation, while still being encompassed by the present disclosure. As noted above, particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific examples disclosed in the specification, unless the above Detailed Description section explicitly defines such terms. Accordingly, the actual scope of the invention encompasses not only the disclosed examples, but also all equivalent ways of practicing or implementing the invention under the claims.

From the foregoing, it will be appreciated that specific embodiments of the invention have been described herein for purposes of illustration, but that various modifications may be made without deviating from the spirit and scope of the various embodiments of the invention. Further, while various advantages associated with certain embodiments of the invention have been described above in the context of those embodiments, other embodiments may also exhibit such advantages, and not all embodiments need necessarily exhibit such advantages to fall within the scope of the invention. Accordingly, the invention is not limited, except as by the appended claims. Although certain aspects of the invention are presented below in certain claim forms, the applicant contemplates the various aspects of the invention in any number of claim forms. Accordingly, the applicant reserves the right to pursue additional claims after filing this application to pursue such additional claim forms, in either this application or in a continuing application.

We claim:

1. A method for detecting a presence or absence of a screen cover on an electronic device, the method comprising:
   receiving an image of a front side of an electronic device, the electronic device having a screen and a non-screen periphery at the front side;
   automatically identifying line segments in a portion of the image corresponding to the non-screen periphery using machine vision;
   determining respective angles of the identified line segments relative to a first axis of the electronic device;
   determining a first amount of the identified line segments having respective angles within a first predetermined range about the first axis;
   determining a second amount of the identified line segments having respective angles within a second predetermined range about a second axis orthogonal to the first axis; and
   determining a presence or absence of a screen cover on the electronic device based at least in part on the first amount, the second amount, or both.

2. The method of claim 1, wherein the first predetermined range extends no more than 5 degrees off the first axis.

3. The method of claim 1, wherein the second predetermined range extends no more than 5 degrees off the second axis.

4. The method of claim 1 wherein automatically identifying the line segments using machine vision includes applying an edge detector algorithm to the image.

5. The method of claim 1 wherein:
   determining the first amount includes determining a first quantity of the identified line segments having respective angles within the first predetermined range; and
   determining the second amount includes determining a second quantity of the identified line segments having respective angles within the second predetermined range.

6. The method of claim 1 wherein:
   determining the first amount includes determining a first extent of the identified line segments having respective angles within the first predetermined range; and determining the second amount includes determining a second extent of the identified line segments having respective angles within the second predetermined range.

7. The method of claim 1 wherein determining the presence or absence of a screen cover on the electronic device includes determining the presence of a screen cover on the electronic device when the first amount, the second amount, or both exceeds a predetermined threshold amount.

8. The method of claim 1 wherein determining the presence or absence of a screen cover on the electronic device includes determining the absence of a screen cover on the electronic device when the first amount, the second amount, or both is less than a predetermined threshold amount.

9. The method of claim 1 wherein:
the identified line segments are first identified line segments;
the portion of the image is a first portion of the image; and
the method further comprises—
   automatically identifying second line segments in a second portion of the image corresponding to the screen of the electronic device using machine vision, and
   determining whether the screen is cracked based at least in part on the identified second line segments and the presence or absence of a screen cover on the electronic device.

10. The method of claim 9, further comprising determining respective positions of the identified second line segments, wherein determining whether the screen is cracked includes determining an amount of the identified second line segments, and wherein determining the amount of the identified second line segments includes giving greater weight to the identified second line segments farther from a perimeter of the second portion of the image than to the identified second line segments closer to the perimeter of the second portion of the image.

11. The method of claim 9, further comprising determining respective angles of the identified second line segments, wherein determining whether the screen is cracked includes determining an amount of the identified second line segments, and wherein determining the amount of the identified second line segments includes giving greater weight to the identified second line segments farther from having the first angle or the second angle than to the identified second line segments closer to having the first angle or the second angle.

12. A method for detecting a presence or absence of a screen cover on an electronic device, the method comprising:
receiving an image of a front side of an electronic device, the electronic device having a screen and a non-screen periphery at the front side, the non-screen periphery having four corner portions;
automatically identifying line segments in the image using machine vision;
determining respective positions of the identified line segments within the image;
determining a first amount of the identified line segments having respective positions within portions of the image corresponding to the corner portions of the non-screen periphery;
determining a second amount of the identified line segments having respective positions not within the portions of the image corresponding to the corner portions of the non-screen periphery; and
determining a presence or absence of a screen cover on the electronic device based at least in part on the first amount relative to the second amount.

13. The method of claim 12 wherein automatically identifying the line segments using machine vision includes applying an edge detector algorithm to the image.

14. The method of claim 12 wherein the corner portions extend no more than 5 cm from a horizontal edge of the electronic device and no more than 5 cm from a vertical edge of the electronic device.

15. A computer-readable memory carrying non-transitory computer-executable instructions for causing one or more processors to facilitate detecting the presence or absence of a screen cover on an electronic device, the computer-executable instructions comprising instructions that, when executed by the one or more processors:
receive an image of a front side of an electronic device, the electronic device having a screen and a non-screen periphery at the front side;
automatically identify line segments in a portion of the image corresponding to the non-screen periphery of the electronic device using machine vision;
determine respective angles of the identified line segments;
determine a first amount of the identified line segments having respective angles within a first predetermined range about a vertical angle;
determine a second amount of the identified line segments having respective angles within a second predetermined range about a horizontal angle; and
determine the presence or absence of a screen cover on the electronic device based at least in part on the first amount, the second amount, or both.

16. The computer-readable memory claim 15 wherein the computer-executable instructions, when executed by the one or more processors, automatically identify the line segments by applying an edge detector algorithm to the image.

17. The computer-readable memory of claim 15 wherein the computer-executable instructions, when executed by the one or more processors, determine the presence of a screen cover on the electronic device when the first amount, the second amount, or both exceeds a predetermined threshold amount.

18. The computer-readable memory of claim 15 wherein:
the identified line segments are first identified line segments;
the portion of the image is a first portion of the image; and
the computer-executable instructions, when executed by the one or more processors—
   automatically identify second line segments in a second portion of the image corresponding to the screen of the electronic device using machine vision, and
   determine whether the screen is cracked based at least in part on the identified second line segments and the presence or absence of a screen cover on the electronic device.

19. The computer-readable memory of claim 15 wherein:
the non-screen periphery has four corner portions; and
the computer-executable instructions, when executed by the one or more processors—
   determine an amount of the identified line segments within portions of the image corresponding to the corner portions of the non-screen periphery, and
   determine the presence or absence of a screen cover on the electronic device based at least in part on the amount of the identified line segments within the portions of the image corresponding to the corner portions of the non-screen periphery.

20. A method for detecting a presence or absence of a screen cover on an electronic device, the method comprising:
receiving an image of a front side of an electronic device;
screening segments of the image for indicia of bubbles;
identifying a number of segments of the image in which indicia of bubbles are present; and
determining a presence or absence of a screen cover on the electronic device based at least in part on the number of segments of the image in which indicia of bubbles are present.

21. The method of claim 20 wherein the segments of the image are parallel slices of the image.

22. The method of claim 20 wherein screening segments of the image for indicia of bubbles comprises, for individual segments of the image:
blurring the segment;
determining a ratio of disproportionally bright pixels to total pixels in the blurred segment; and
if the ratio exceeds a predetermined threshold, identifying indicia of bubbles in the segment.

23. The method of claim 22, wherein:
screening segments of the image for indicia of bubbles further comprises, for individual segments of the image, determining a standard deviation of brightness within the segment; and
identifying indicia of bubbles in the segment includes identifying indicia of bubbles in the segment if the standard deviation falls within a predetermined range.

24. The method of claim 23 wherein the predetermined range includes a range between about 4 and about 40 brightness units.

25. The method of claim 22 wherein the disproportionally bright pixels comprise pixels of brightness exceeding an average brightness of the blurred segment by at least a predetermined threshold amount.

26. The method of claim 25 wherein the predetermined threshold amount is at least 5%.

* * * * *